US012655380B2

(12) United States Patent (10) Patent No.: US 12,655,380 B2
Hagiwara (45) Date of Patent: Jun. 16, 2026

(54) FLUIDIC DEVICE

(71) Applicant: UNIVERSITY PUBLIC CORPORATION OSAKA, Osaka (JP)

(72) Inventor: Masaya Hagiwara, Sakai (JP)

(73) Assignee: UNIVERSITY PUBLIC CORPORATION OSAKA, Osaka (JP)

( * ) Notice: Subject to any disclaimer, the term of this patent is extended or adjusted under 35 U.S.C. 154(b) by 1043 days.

(21) Appl. No.: 17/440,996

(22) PCT Filed: Mar. 16, 2020

(86) PCT No.: PCT/JP2020/011482
    § 371 (c)(1),
    (2) Date: Sep. 20, 2021

(87) PCT Pub. No.: WO2020/189627
    PCT Pub. Date: Sep. 24, 2020

(65) Prior Publication Data
    US 2022/0169970 A1 Jun. 2, 2022

(30) Foreign Application Priority Data
    Mar. 20, 2019 (JP) ................................. 2019-053203

(51) Int. Cl.
    *C12M 1/00* (2006.01)
    *C12M 1/12* (2006.01)
    (Continued)

(52) U.S. Cl.
    CPC ............ *C12M 29/04* (2013.01); *C12M 23/38* (2013.01); *C12M 23/44* (2013.01); *C12M 25/00* (2013.01); *C12M 29/10* (2013.01); *C12M 41/00* (2013.01)

(58) Field of Classification Search
    CPC ....... B01L 3/5027; C12M 23/16; C12M 23/44
    See application file for complete search history.

(56) References Cited

U.S. PATENT DOCUMENTS

2010/0273200 A1    10/2010 Niwa et al.
2014/0057311 A1*   2/2014 Kamm ............... G01N 33/5029
                                                216/33
(Continued)

FOREIGN PATENT DOCUMENTS

JP        2007-166915 A     7/2007
WO    WO-2017035119 A1 *  3/2017    ............ C12M 23/16
(Continued)

OTHER PUBLICATIONS

Hagiwara et al. Tissue in Cube: In Vitro 3D Culturing Platform with Hybrid Gel Cubes for Multidirectional Observations. Adv Healthcare Mater 5: 1566-1571. (Year: 2016).*
(Continued)

*Primary Examiner* — James D Schultz
*Assistant Examiner* — Keenan A Bates
(74) *Attorney, Agent, or Firm* — Stites & Harbison, PLLC; Jeffrey A. Haeberlin; Patrick M. Torre

(57) ABSTRACT

A fluidic device according to the present invention includes a base and a lid member. The base and the lid member are configured to form a first flow path, a second flow path, and a third flow path between the base and the lid member, the base and the lid member being bonded to each other, the first flow path communicating with the second flow path through the third flow path. The third flow path has a first accommodation section for detachably accommodating a first cell culture module. The second flow path has a second accommodation section for detachably accommodating a second cell culture module. The first cell culture module contains first cells having a barrier function and a first culture gel. The second cell culture module contains second cells and a second culture gel. The first accommodation section is configured in such a manner that the first cell culture module blocks the third flow path.

12 Claims, 15 Drawing Sheets

(51) Int. Cl.
　　*C12M 1/34*　　　　(2006.01)
　　*C12M 3/00*　　　　(2006.01)

(56) References Cited

U.S. PATENT DOCUMENTS

2020/0017814 A1　1/2020　Hagiwara et al.
2020/0032186 A1　1/2020　Hagiwara

FOREIGN PATENT DOCUMENTS

WO　　2018/147032 A1　8/2018
WO　　2018/150689 A1　8/2018

OTHER PUBLICATIONS

Adriani et al. A 3D neurovascular microfluidic model consisting of neurons, astrocytes and cerebral endothelial cells as a blood-brain barrier. Lab Chip 17: 448-459. (Year: 2017).*

Sofroniew et al. Astrocyte barriers to neurotoxic inflammation. Nat Rev Neurosci 16: 249-263. (Year: 2015).*

Zhou et al. The recent development and applications of fluidic channels by 3D printing. Journal of Biomedical Science 24: 1-22. (Year: 2017).*

Abhyankar et al. A Reversibly Sealed, Easy Access, Modular (SEAM) Microfluidic Architecture to Establish In Vitro Tissue Interfaces. PLoS One 11: 1-20. (Year: 2016).*

Campisi et al. 3D self-organized microvascular model of the human blood-brain barrier with endothelial cells, pericytes and astrocytes. Biomaterials 180: 117-129. (Year: 2018).*

Hagiwara, M., et al. "Tissue in Cube: In Vitro 3D Culturing Platform with Hybrid Gel Cubes for Multidirectional Observations," Advanced Healthcare Materials, 2016, 5, 1566-1571. See ISR for relevance.

Nobata, Rina et al., "Elucidation of branch pattern formation by in vitro-in silico interface with 3D culture platform." Programs and abstracts of the annual meeting of the molecular biology society of Japan, 2018, 3AW-06-7 (3P-0355). English translation not available. See ISR for relevance.

Japan Patent Office, International Search Report issued in corresponding Application No. PCT/JP2020/011482, mailed Jun. 9, 2020.

European Patent Office, Extended European Search Report issued in corresponding Application No. 20773056.5, dated May 31, 2023.

* cited by examiner

[FIG. 1]
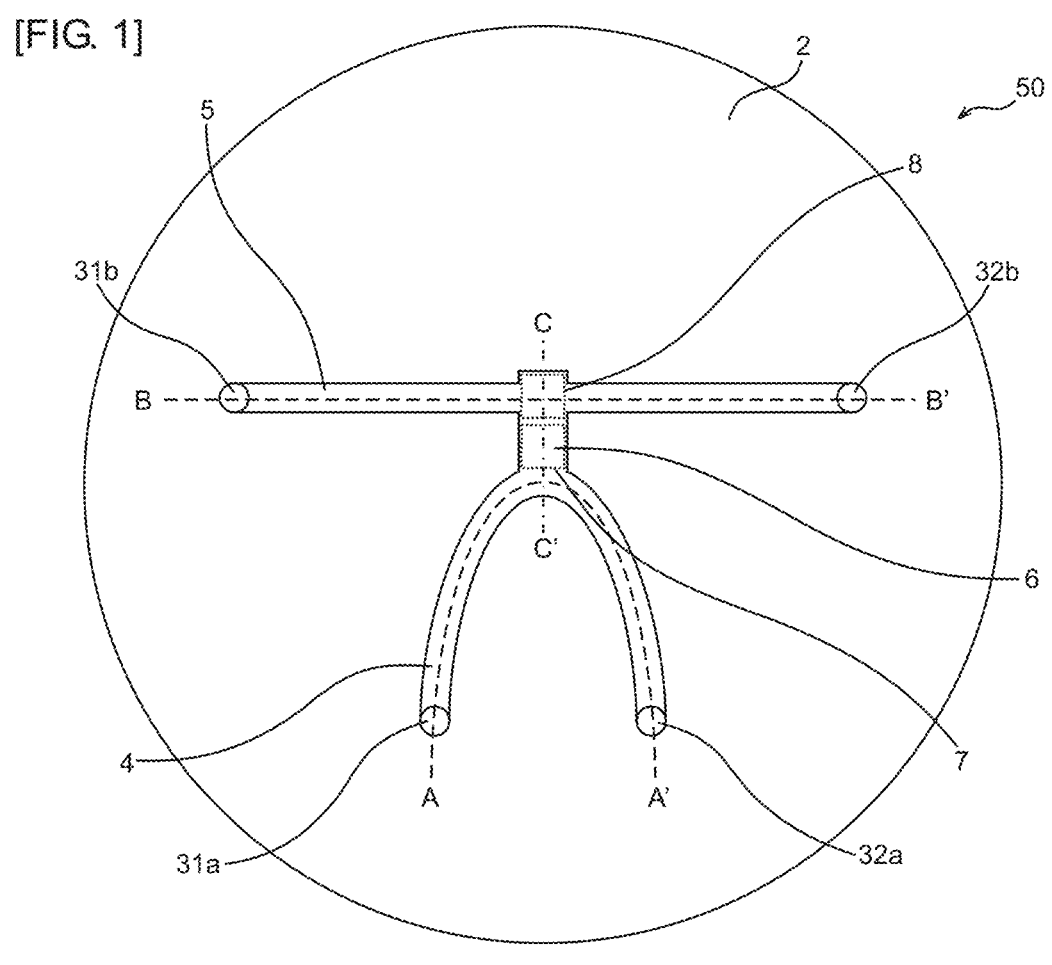
[FIG. 2]
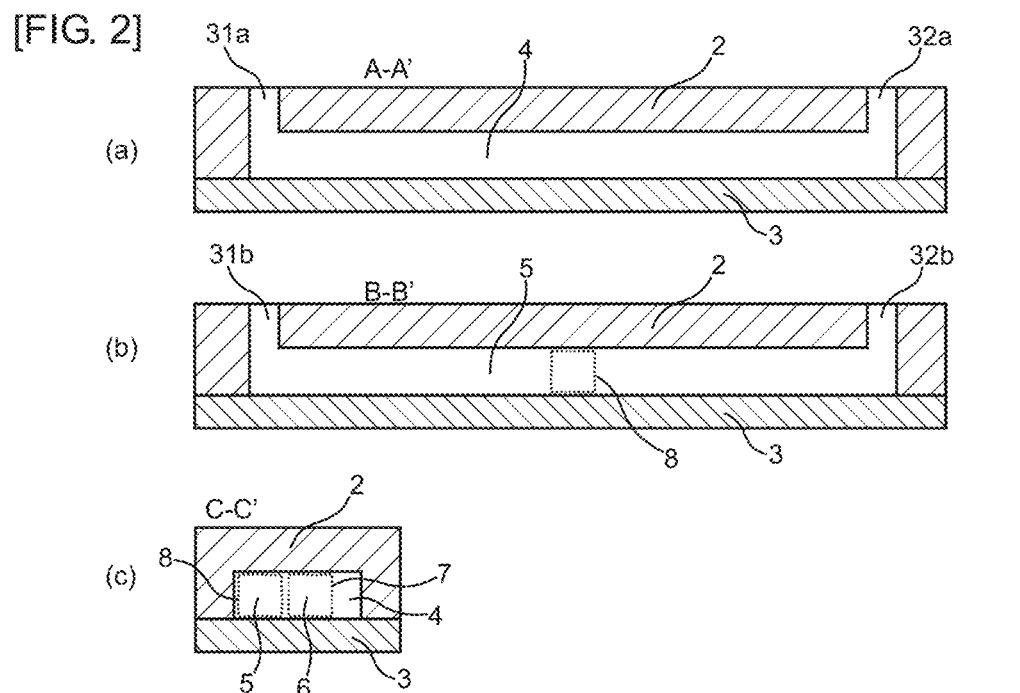

[FIG. 3]
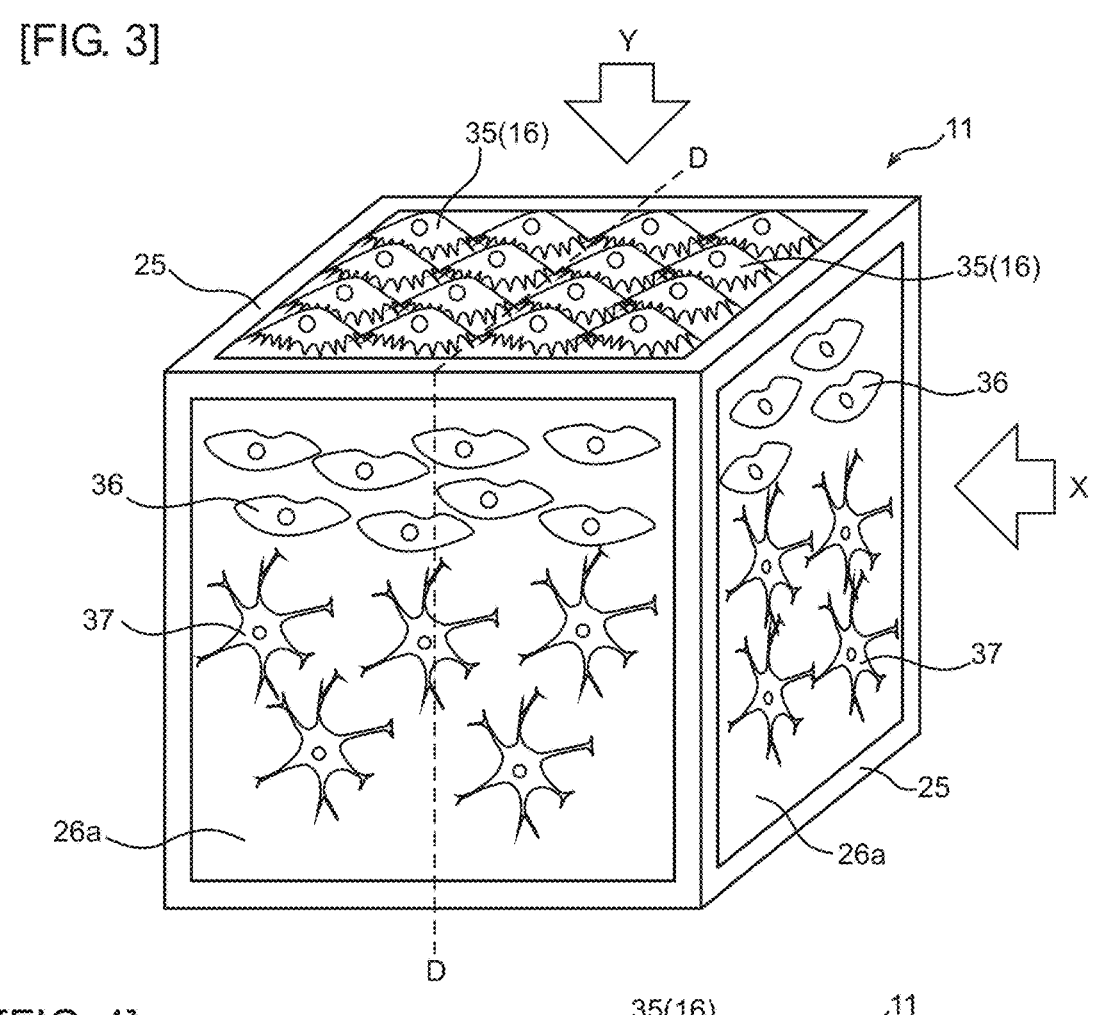
[FIG. 4]
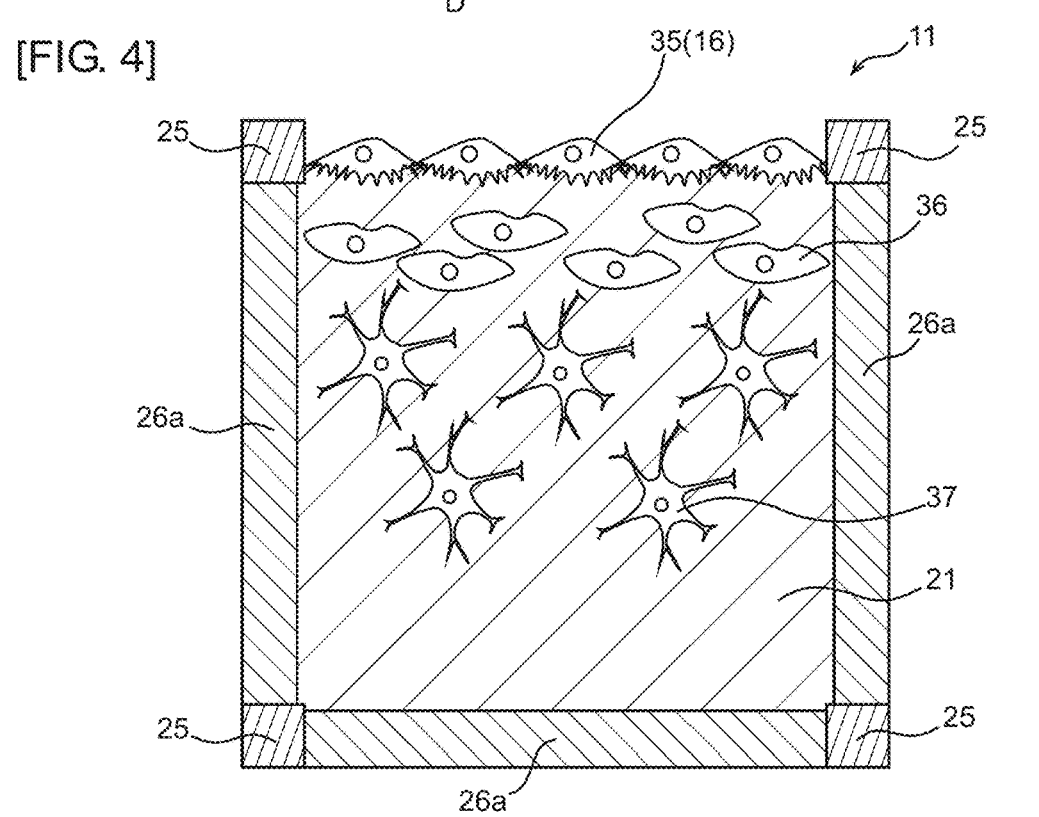

[FIG. 5]
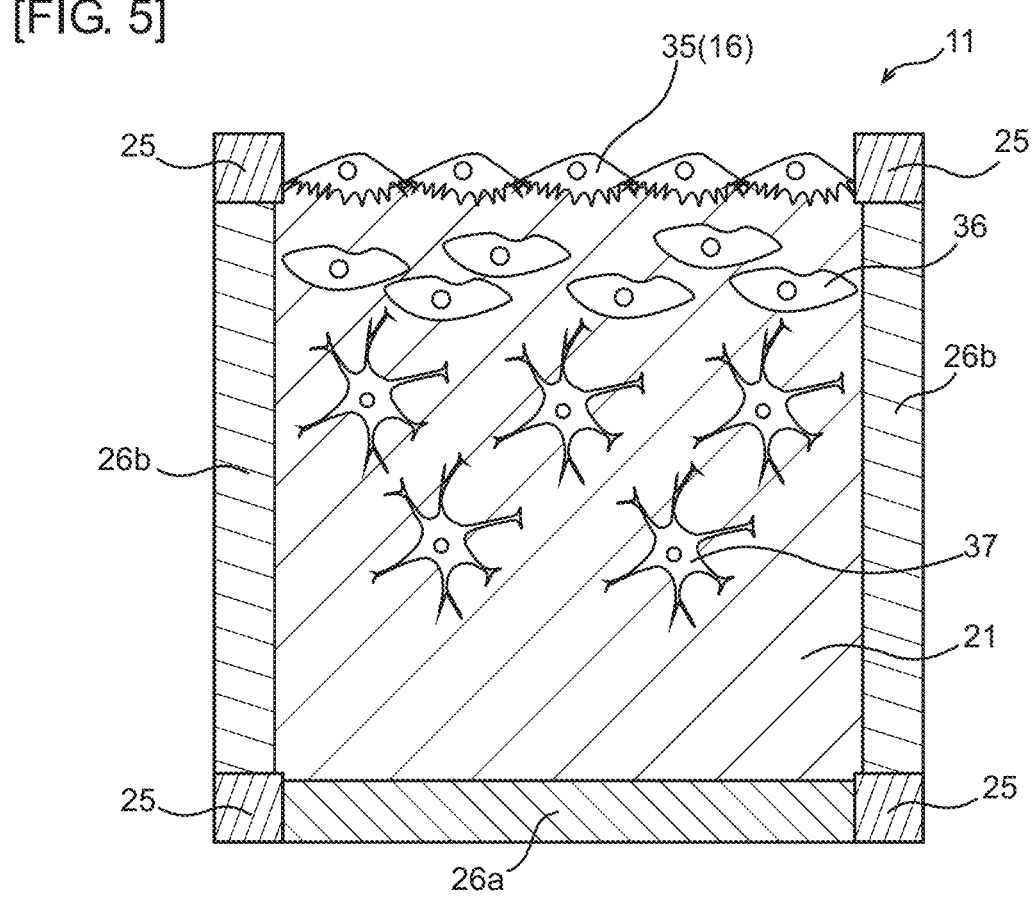

[FIG. 6]
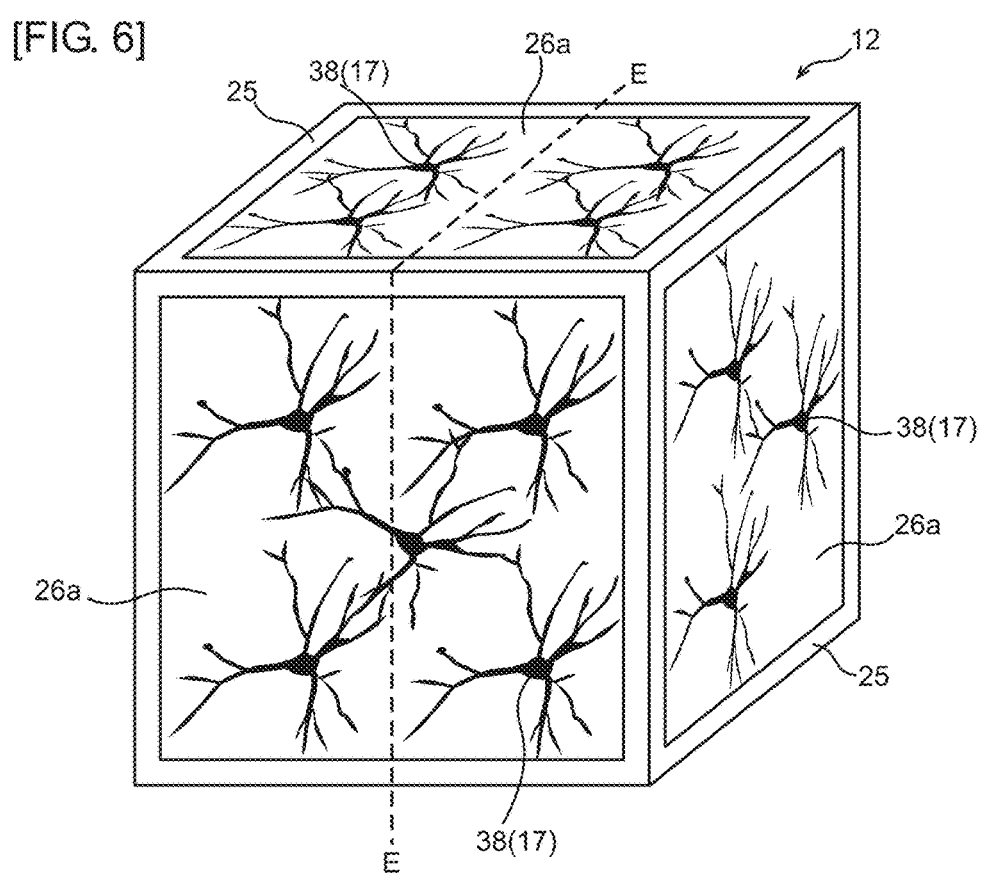
[FIG. 7]
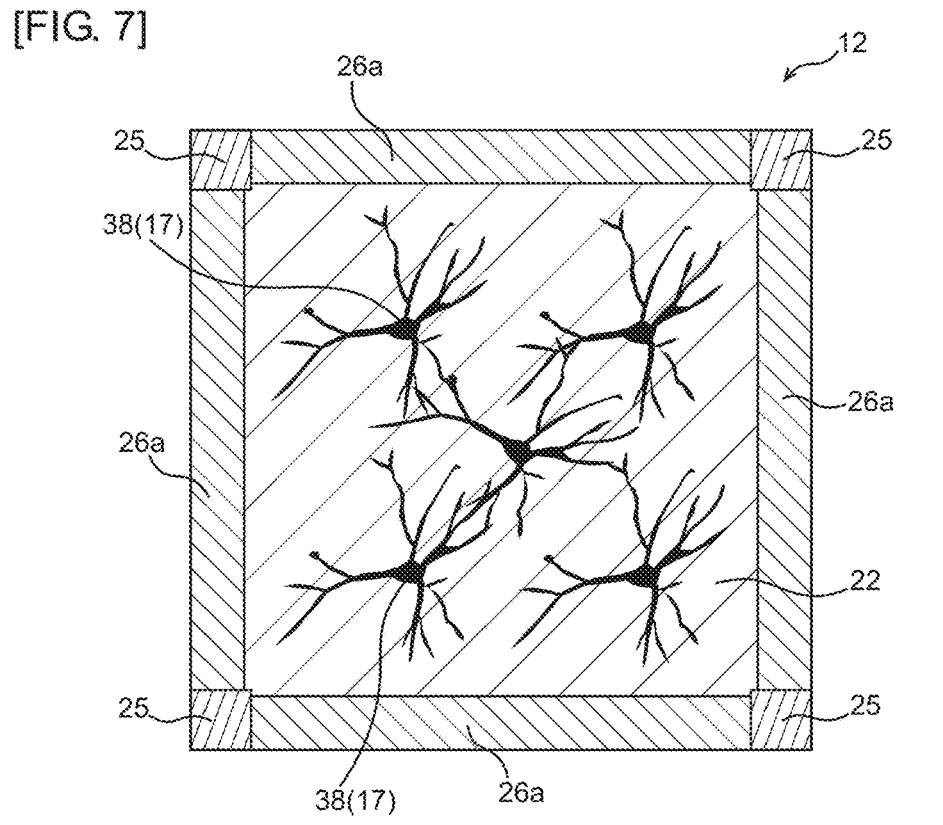

[FIG. 8]
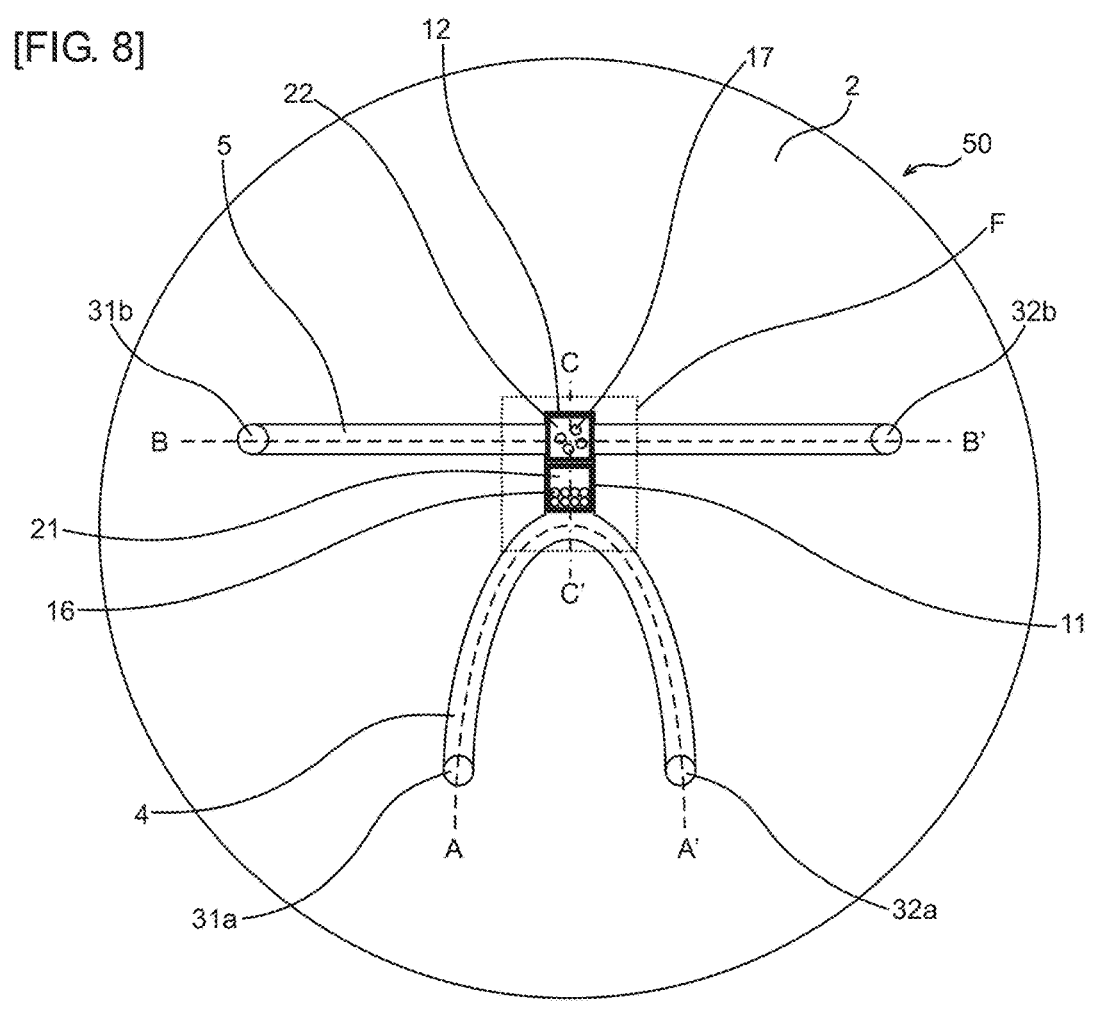
[FIG. 9]
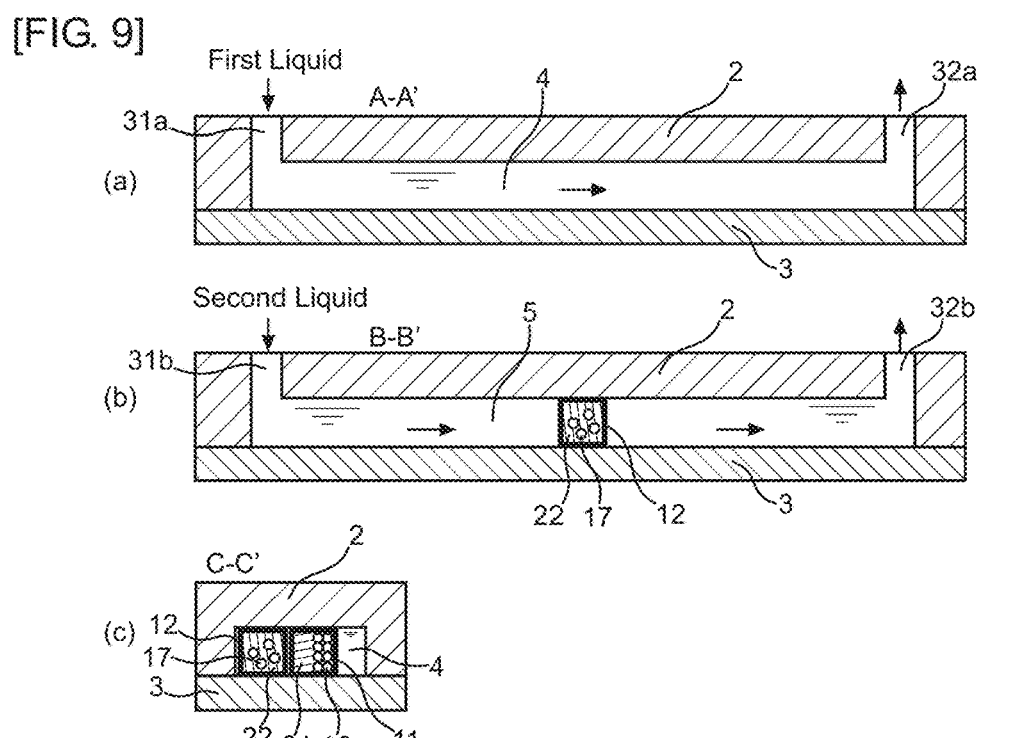

[FIG. 10]
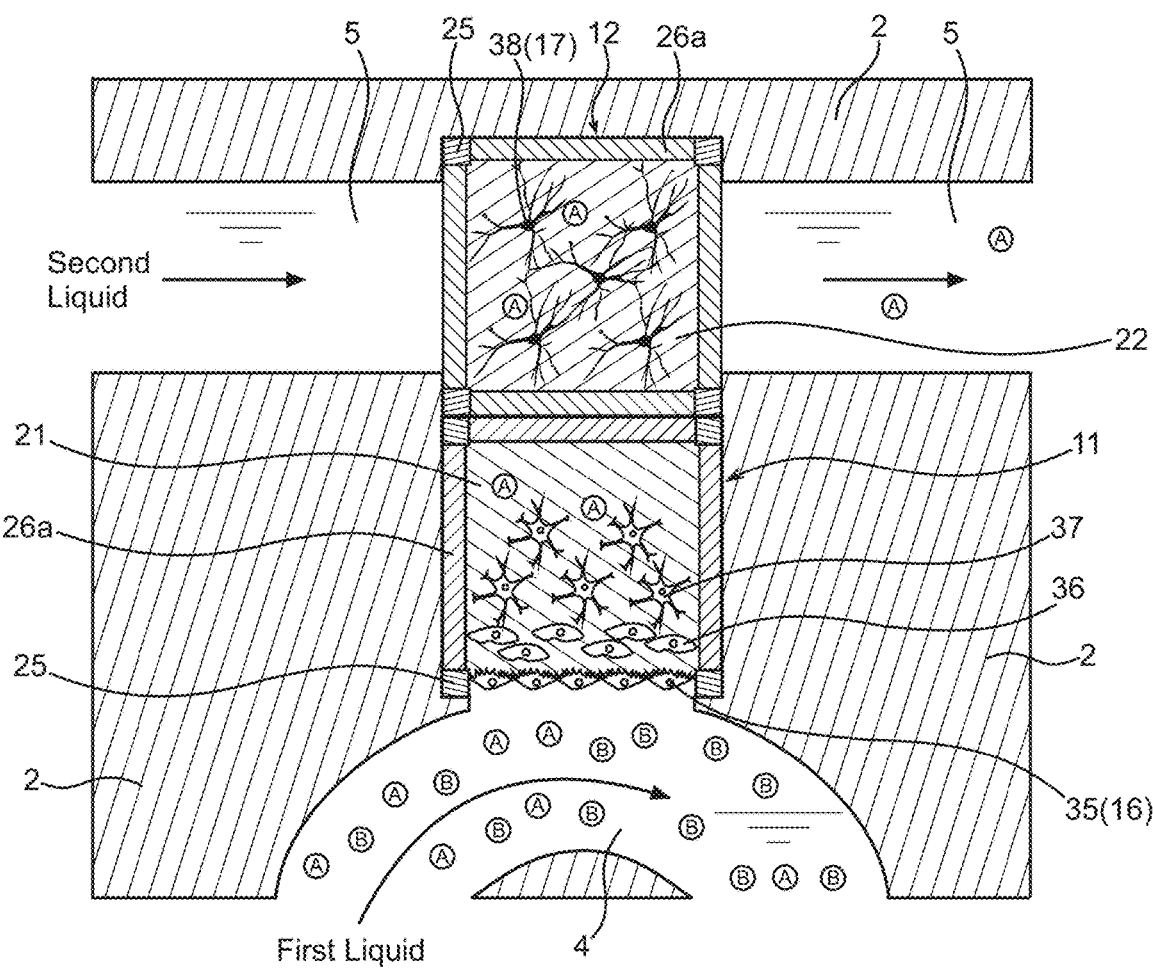

[FIG. 11]
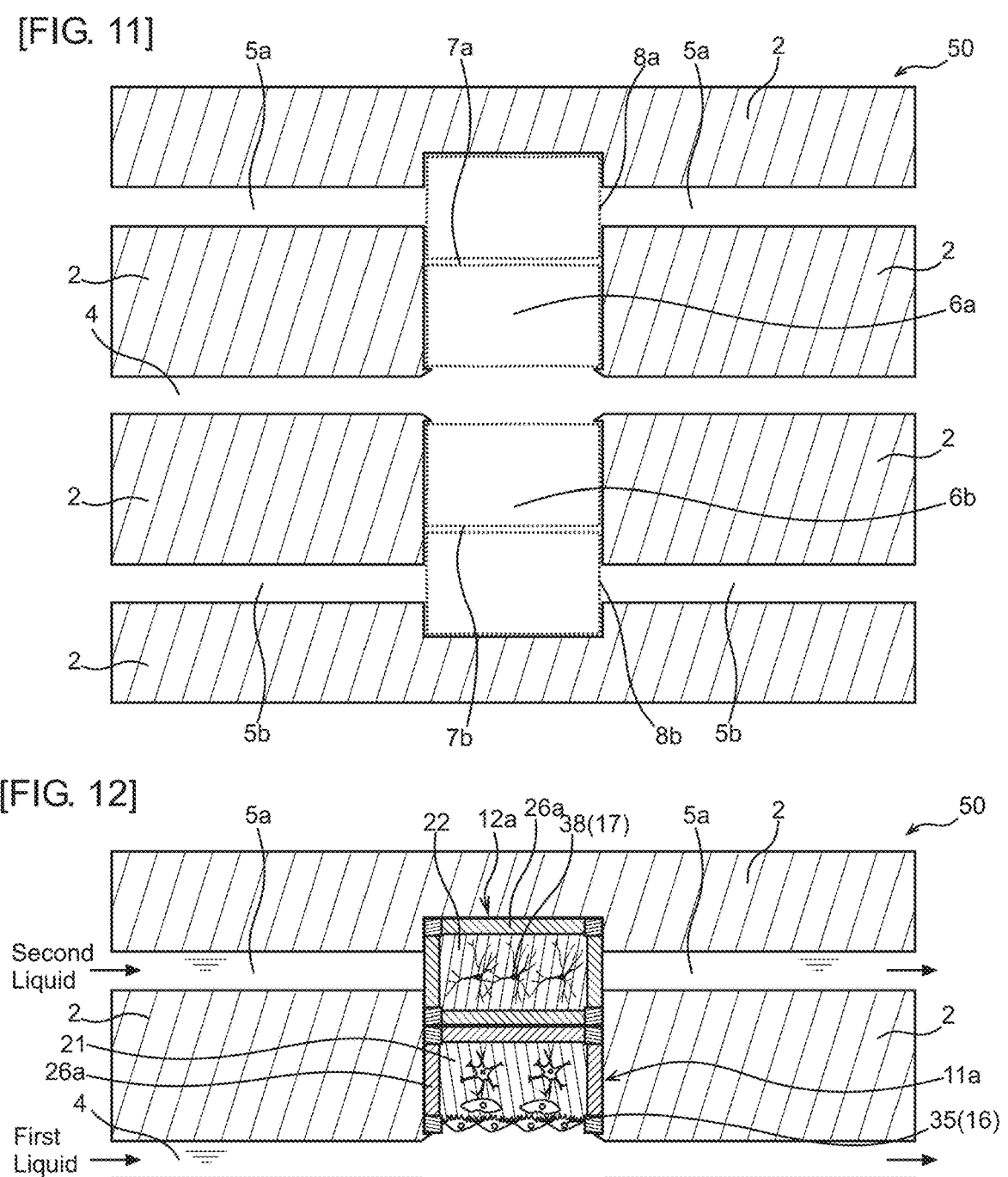
[FIG. 12]

[FIG. 13]
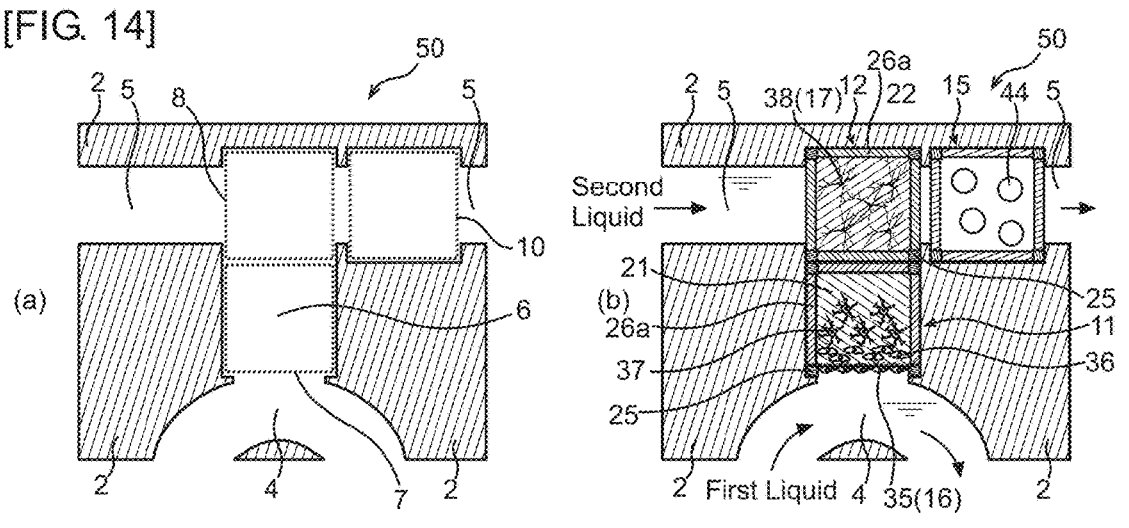
[FIG. 14]

[FIG. 15]
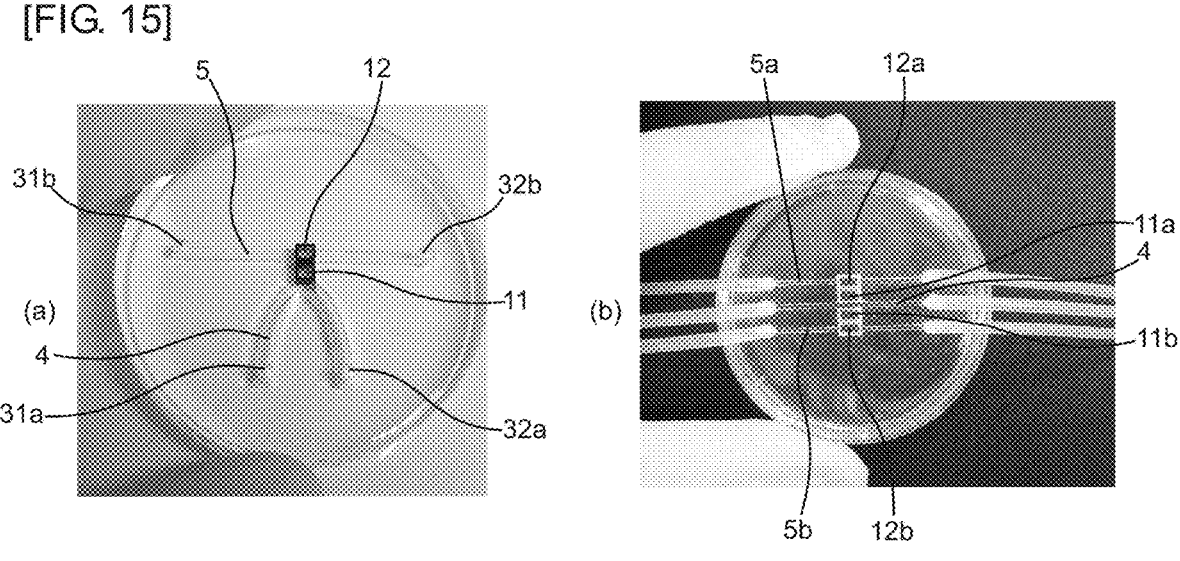
[FIG. 16]
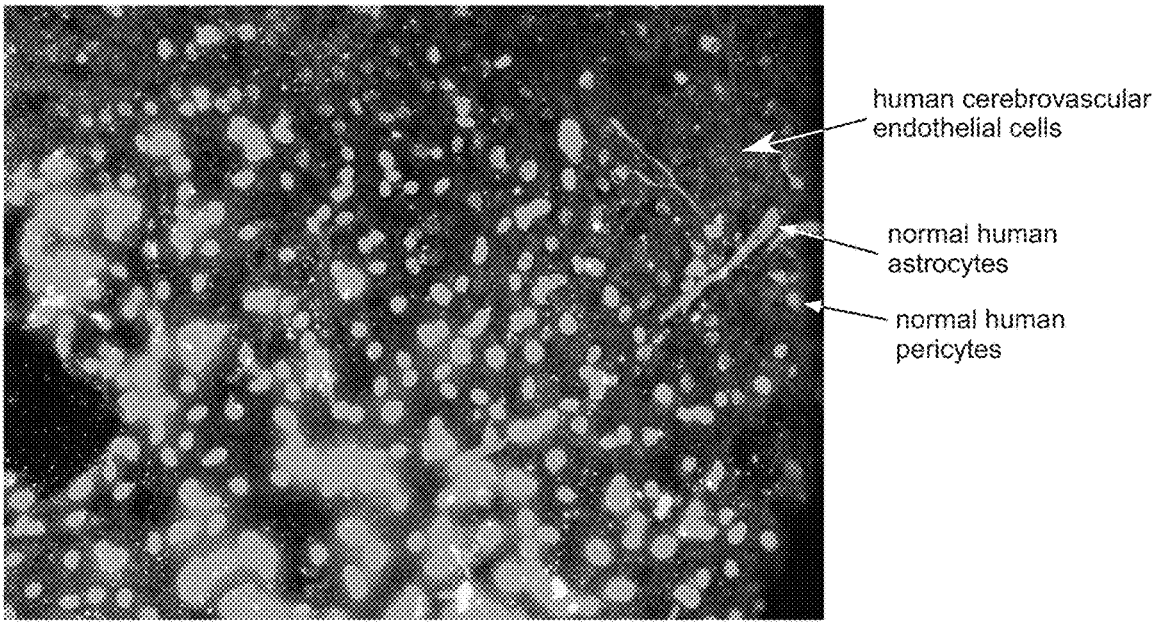

[FIG. 17]
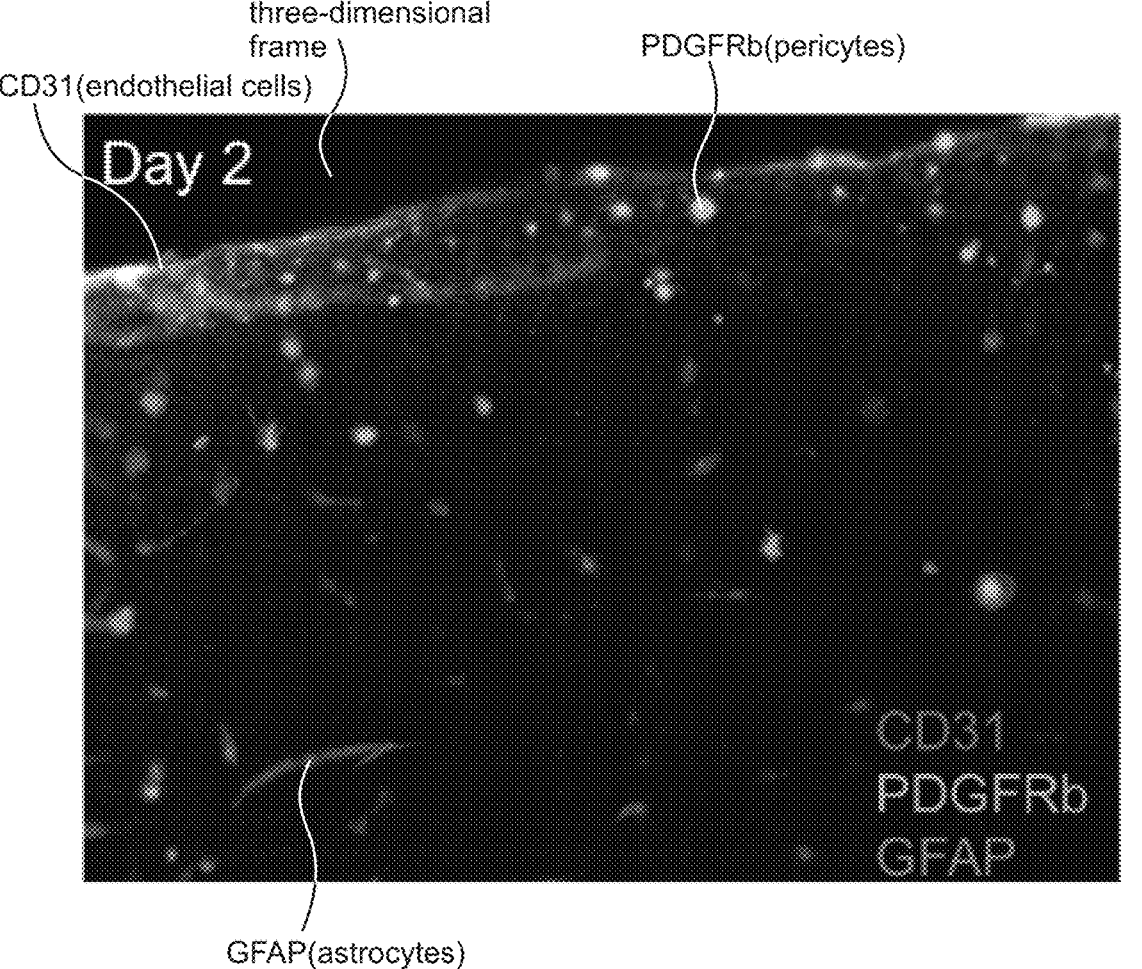
[FIG. 18]

[FIG. 19]
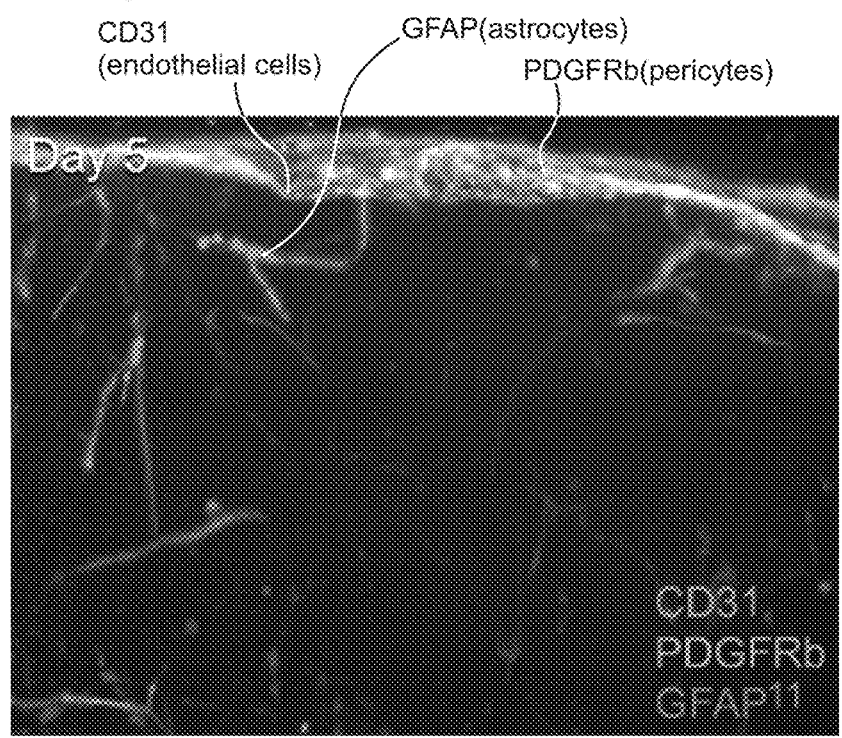
[FIG. 20]
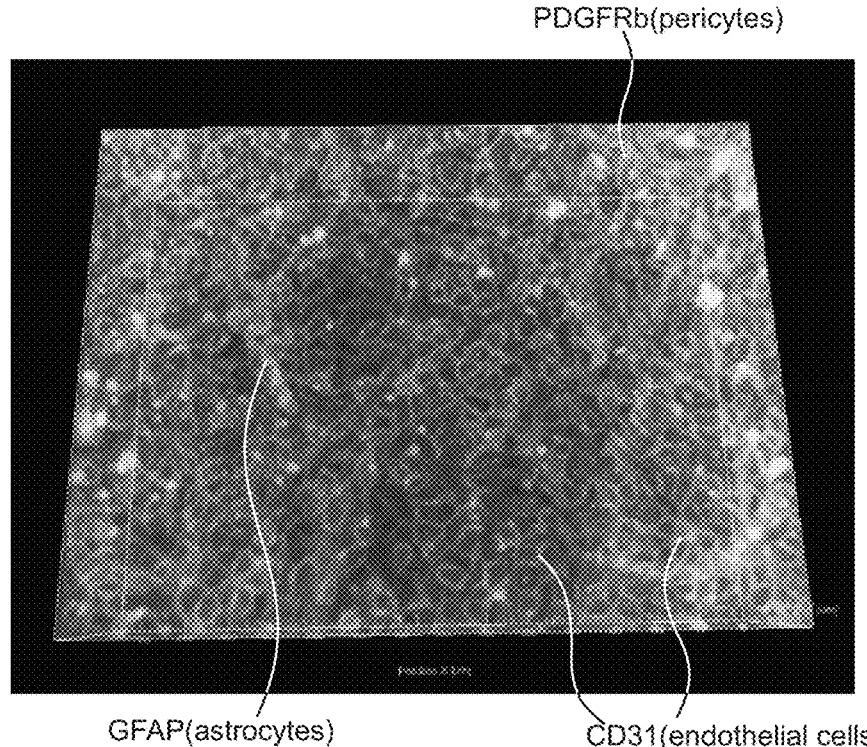

[FIG. 21]
GLUT1
BCRP
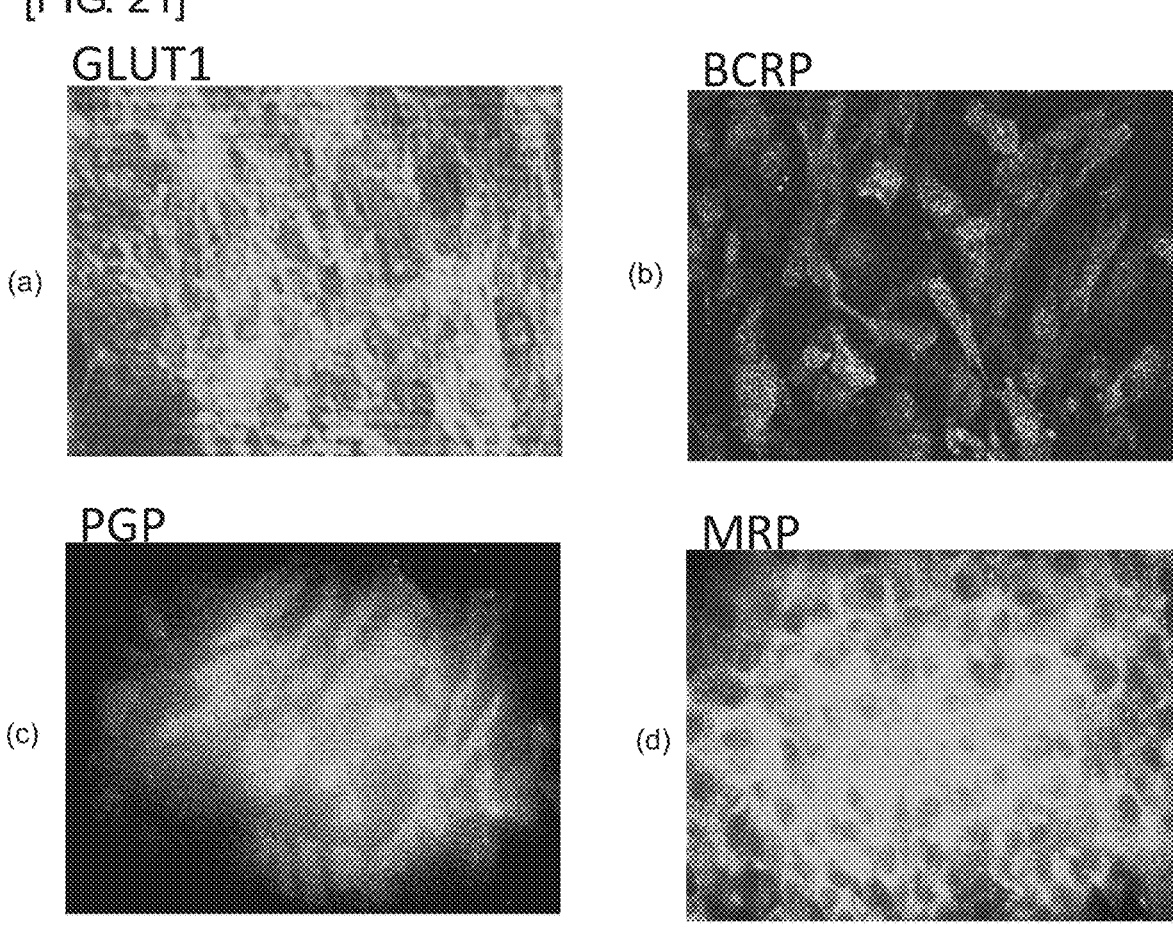
(a)
(b)
PGP
MRP
(c)
(d)
MCT
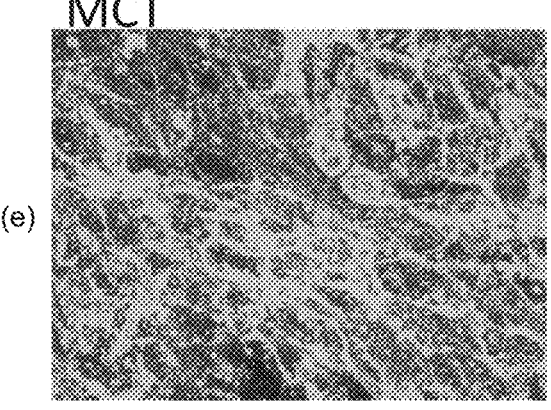
(e)

[FIG. 22]
ZO-1
(a)
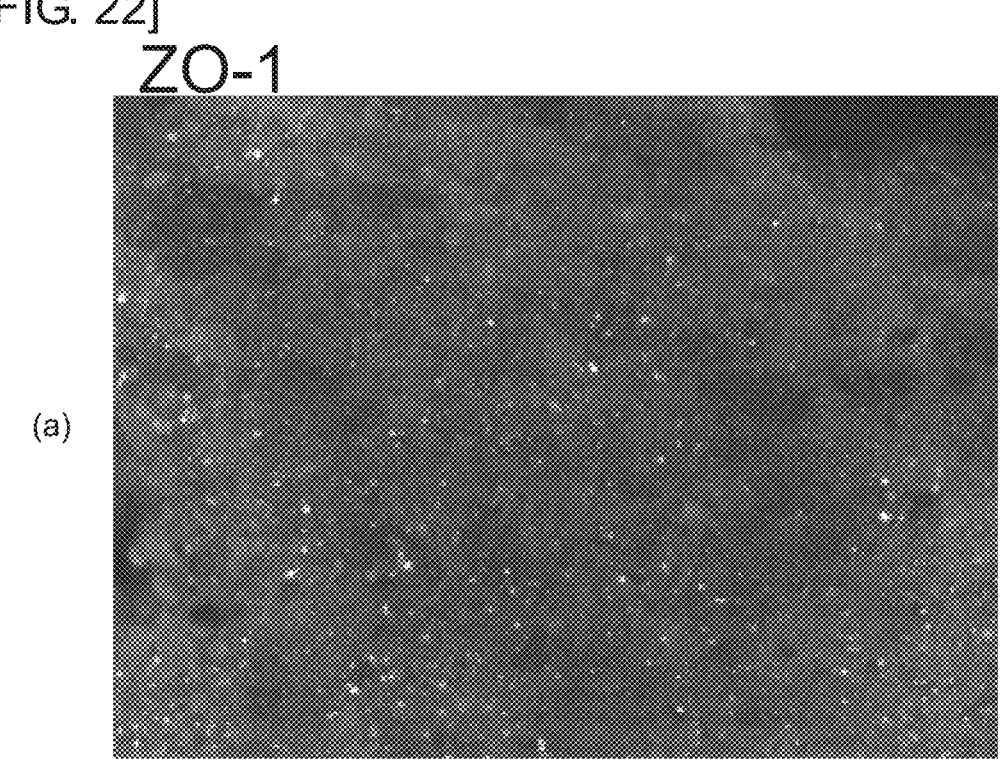
ZO-1
(b)
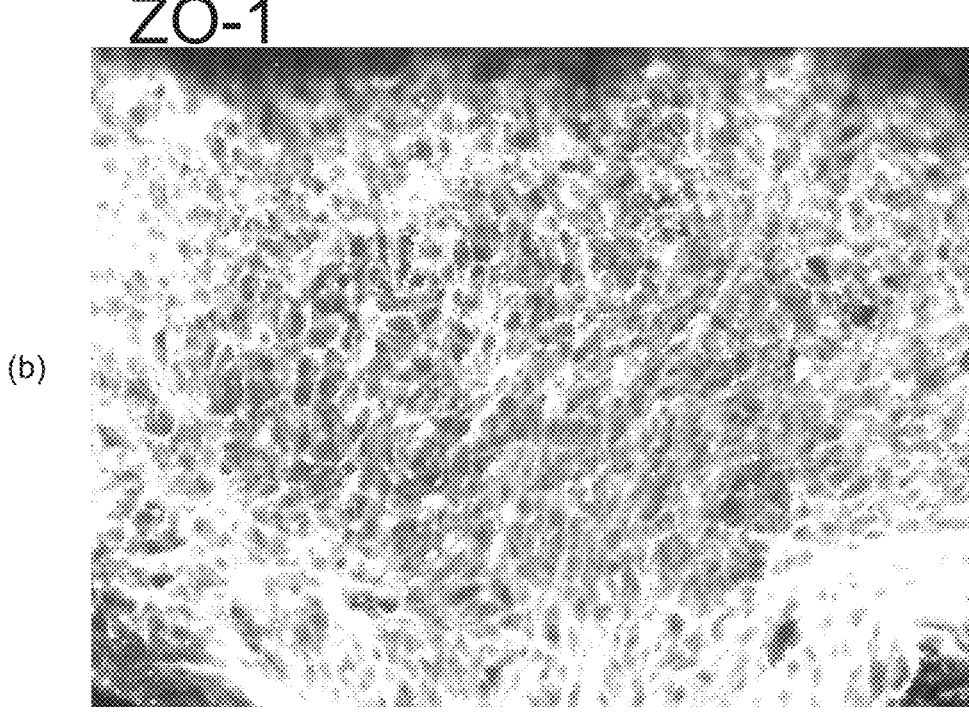

[FIG. 23]
(a) 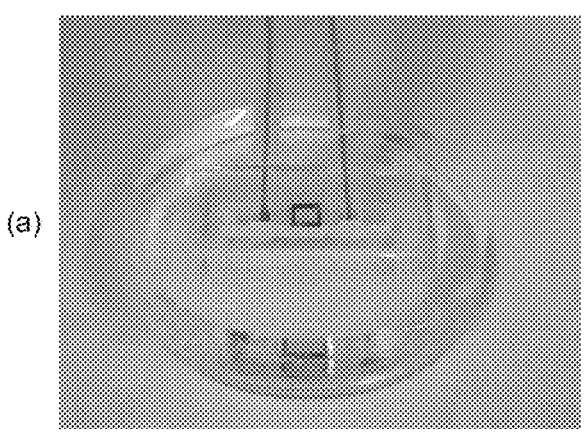    (b)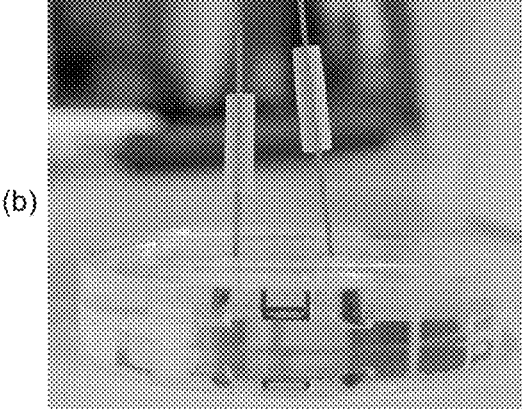
[FIG. 24]
fluorescence image    phase-contrast image
+
fluorescence image
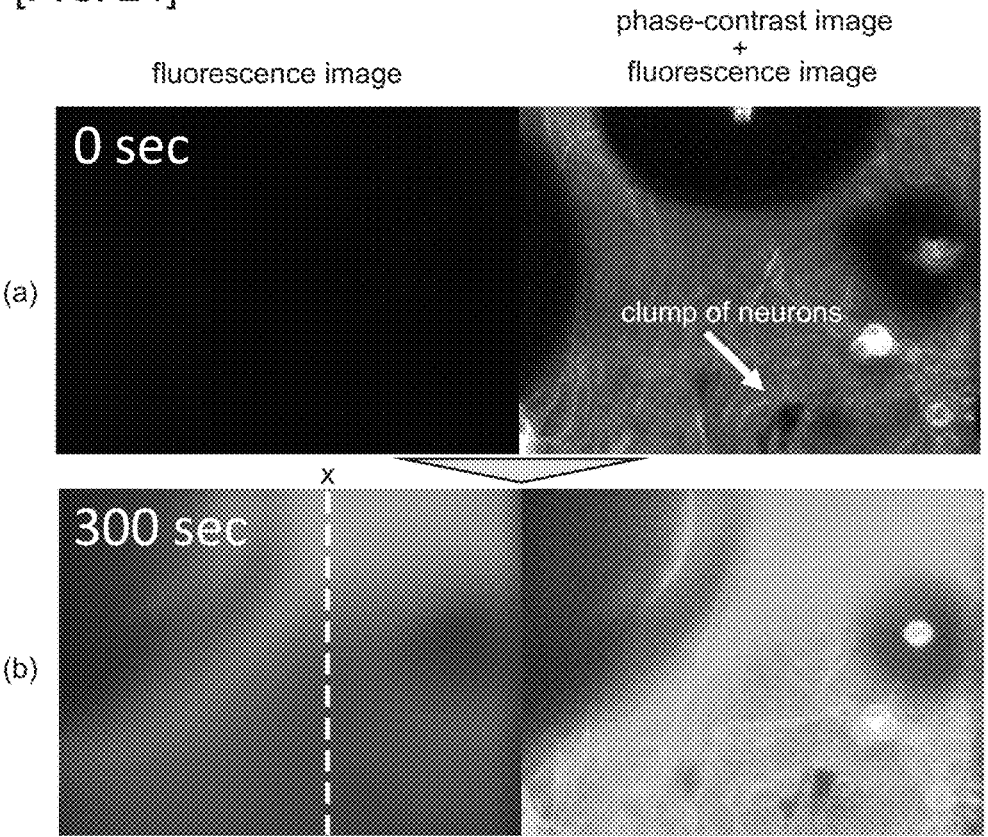
(a) 0 sec    clump of neurons
(b) 300 sec

[FIG. 25]
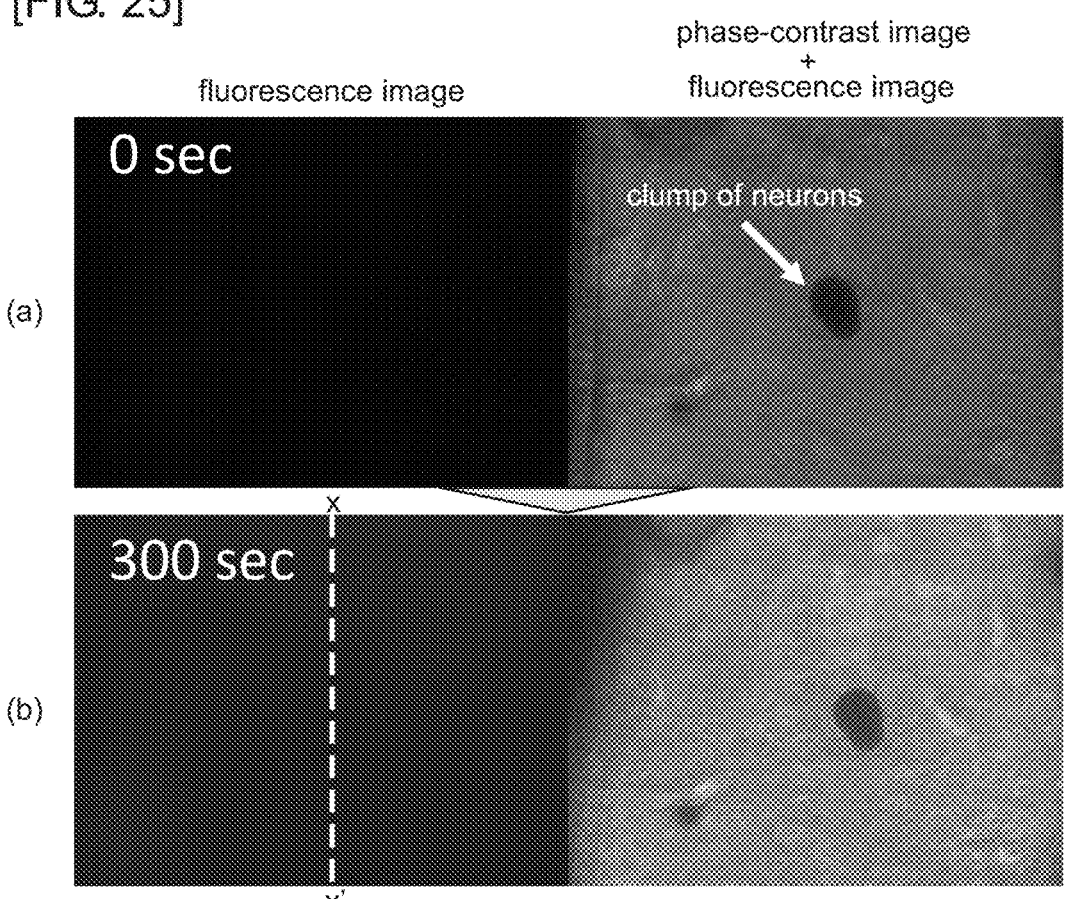
[FIG. 26]
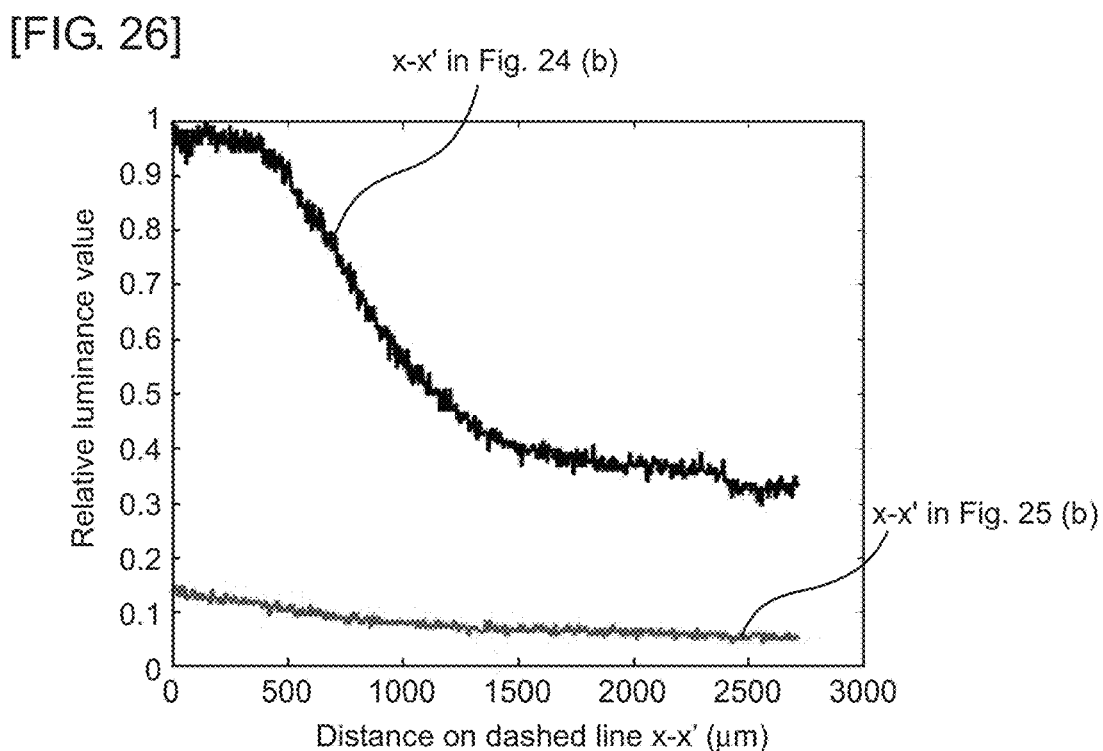

FLUIDIC DEVICE

TECHNICAL FIELD

The present invention relates to a fluidic device.

BACKGROUND ART

Living bodies have cellular tissues that have a barrier function for retaining biological functions thereof. For example, skin has epidermal cells that keep foreign substances from entering the body. Some cellular tissues that have the barrier function further have a selective uptake mechanism (filtering function). For example, the blood-brain barrier and the blood-retinal barrier have vascular endothelial cells that are bound through strong intercellular adhesion, and these endothelial cells have the barrier function and the selective uptake mechanism. Intestines have intestinal epithelial cells that have a mechanism for selectively absorbing nutrients. Kidneys produce urine through a two-step system including glomerular filtration and tubular reabsorption, and tubules have tubular cells that have a mechanism for transporting only specific substances.

The barrier function and the selective uptake mechanism of these cellular tissues have been studied in various fields such as pathology, medicine, functional foods, and cosmetics. In these studies, the barrier function and the uptake mechanism are mainly evaluated through animal experiments and clinical trials. However, it is difficult to accurately evaluate only the barrier function and the uptake mechanism in complex living bodies through animal experiments and clinical trials. Furthermore, from the perspective of animal protection, development of laws and regulations for animal experiments is progressing worldwide. Research and development of alternatives to animal experiments are therefore being actively pursued around the world.

An in vitro model of the blood-brain barrier is known (see, for example, Patent Document 1). The barrier function and the selective uptake mechanism of the blood-brain barrier can be evaluated using such an in vitro model.

Also known is a fluidic chip for detachably accommodating a cube-shaped culture vessel having a window that allows nutrients and the like to pass therethrough (see, for example, Patent Document 2).

CITATION LIST

Patent Document

Patent Document 1: Japanese Unexamined Patent Application Publication No. 2007-166915
Patent Document 2: WO 2018/147032 A1

SUMMARY OF THE INVENTION

Problem to be Solved by the Invention

Conventional in vitro models of the blood-brain barrier only allow for evaluation of the barrier function and the selective uptake mechanism of the blood-brain barrier, and do not allow for study of how a substance that has passed through the blood-brain barrier affects cells such as neurons, or study of how a humoral factor secreted by cells forming the blood-brain barrier affects cells such as neurons.

The present invention was made in view of such circumstances and provides a fluidic device that makes it possible to study an effect that a test substance having passed through cells or a cellular tissue having a barrier function or a humoral factor secreted by cells in a first cell culture module has on cells inside the barrier.

Means for Solving the Problems

The present invention provides a fluidic device characterized by including a base and a lid member, wherein the base and the lid member are configured to form, between the base and the lid member, a first flow path, a second flow path, and a third flow path through the base and the lid member being bonded to each other, the third flow path connecting the first flow path and the second flow path, the third flow path has a first accommodation section for detachably accommodating a first cell culture module, the second flow path has a second accommodation section for detachably accommodating a second cell culture module, the first cell culture module contains first cells having a barrier function and a first culture gel, and has a light-permeable first window formed from a hydrogel or a porous body, the second cell culture module contains second cells and a second culture gel, and has a light-permeable second window formed from a hydrogel or a porous body, and the first accommodation section allows the first cell culture module to block the third flow path.

Effect of the Invention

A fluidic device according to the present invention has the third flow path connecting the first flow path and a second flow path. The first accommodation section allows the first cell culture module to block the third flow path. By attaching the first cell culture module containing the first cells having the barrier function to the first accommodation section in this fluidic device, it is possible to separate a liquid flowing through the first flow path from a liquid flowing through the second flow path using the first cells having the barrier function or a cellular tissue containing the first cells. Thus, it is possible to form a biological environment model reproducing the inside and the outside of a barrier of a barrier model containing the first cells. Furthermore, it is possible to study the barrier performance of the first cells having the barrier function or the cellular tissue containing the first cells in the first cell culture module by causing a liquid containing a test substance to flow through the first flow path and analyzing the liquid flowing through the second flow path for the presence of the test substance.

The first cell culture module has the first window formed from a hydrogel or a porous body. Through this window, nutrients, a test substance, a humoral factor, or the like can migrate between the first culture gel inside the first cell culture module and a liquid outside the first cell culture module. Thus, it is possible to supply the nutrients to the cellular tissue being three-dimensionally cultured in the first culture gel, it is possible to allow the test substance that has passed through the first cells having the barrier function or the cellular tissue containing the first cells to move to the second flow path, or it is possible to allow the humoral factor produced by the cells in the first cell culture module due to an effect of the test substance to move to the second flow path.

The fluidic device according to the present invention has the second accommodation section for detachably accommodating the second cell culture module. By attaching the second cell culture module including the second cells to the second accommodation section in this fluidic device, it is possible to study, for example, an effect, on the second cells, of a test substance that has passed through the first cells having the barrier function or the cellular tissue containing the first cells in the first cell culture module, or an effect, on the second cells, of a humoral factor produced by the cells in the first cell culture module.

According to the fluidic device of the present invention, the first cell culture module is detachable from the first accommodation section, and the second cell culture module is detachable from the second accommodation section. As such, it is possible to three-dimensionally observe the cells in the first cell culture module or the cells in the second cell culture module through the light-permeable window. It is therefore possible to closely study an effect of a test substance, a humoral factor, or the like on the cells in the first cell culture module or the cells in the second cell culture module.

BRIEF DESCRIPTION OF THE DRAWINGS

FIG. 1 is a schematic plan view of a fluidic device according to an embodiment of the present invention.

FIG. 2(*a*) is a schematic cross-sectional view of the fluidic device taken along a dashed line A-A' in FIG. 1.

FIG. 2(*b*) is a schematic cross-sectional view of the fluidic device taken along a dashed line B-B' in FIG. 1.

FIG. 2(*c*) is a schematic cross-sectional view of the fluidic device taken along a dashed and dotted line C-C' in FIG. 1.

FIG. 3 is a schematic perspective view of a first cell culture module.

FIG. 4 is a schematic cross-sectional view of the first cell culture module taken along a dashed line D-D in FIG. 3.

FIG. 5 is a schematic cross-sectional view of the first cell culture module.

FIG. 6 is a schematic perspective view of a second cell culture module.

FIG. 7 is a schematic cross-sectional view of the second cell culture module taken along a dashed line E-E in FIG. 6.

FIG. 8 is a schematic plan view of a fluidic device according to an embodiment of the present invention.

FIG. 9(*a*) is a schematic cross-sectional view of the fluidic device taken along a dashed line A-A' in FIG. 8.

FIG. 9(*b*) is a schematic cross-sectional view of the fluidic device taken along a dashed line B-B' in FIG. 8.

FIG. 9(*c*) is a schematic cross-sectional view of the fluidic device taken along a dashed and dotted line C-C' in FIG. 8.

FIG. 10 is a schematic cross-sectional view of the fluidic device in a range F enclosed by a dotted line in FIG. 8.

FIG. 11 is a schematic cross-sectional view of a fluidic device according to an embodiment of the present invention.

FIG. 12 is a schematic cross-sectional view of a fluidic device according to an embodiment of the present invention.

FIGS. 13(*a*) to 13(*c*) are each a schematic cross-sectional view of a fluidic device according to an embodiment of the present invention.

FIGS. 14(*a*) and 14(*b*) are each a schematic cross-sectional view of a fluidic device according to an embodiment of the present invention.

FIGS. 15(*a*) and 15(*b*) are each an image of a fluidic device produced in an experiment.

FIG. 16 is an image of a blood-brain barrier model formed in a first cell culture module.

FIGS. 17(*a*) and 17(*b*) are each an image of an interface between a culture gel and a window of a cell culture module.

FIG. 18 is an image of a cell culture module fluorescently captured from the side.

FIG. 19 is an image of the cell culture module fluorescently captured from the side.

FIG. 20 is an image of the cell culture module captured from above.

FIGS. 21(*a*) to 21(*e*) are each a fluorescence image of an immunostained transporter.

FIGS. 22(*a*) and 22(*b*) are each a fluorescence image of an immunostained tight junction marker.

FIGS. 23(*a*) and 23(*b*) are each an image of a TEER measurement vessel having a cell culture module therein.

FIGS. 24(*a*) and 24(*b*) each show images of the inside of a cell culture module including neurons used in a control experiment.

FIGS. 25(*a*) and 25(*b*) each show images of the inside of a cell culture module including neurons used in an experiment for evaluation of a barrier function of a BBB model.

FIG. 26 is a graph showing relative luminance values on dashed lines x-x' in FIGS. 24(*b*) and 25(*b*).

EMBODIMENTS OF THE INVENTION

A fluidic device according to the present invention is characterized by including a base and a lid member, wherein the base and the lid member are configured to form, between the base and the lid member, a first flow path, a second flow path, and a third flow path through the base and the lid member being bonded to each other, the third flow path connecting the first flow path and the second flow path, the third flow path has a first accommodation section for detachably accommodating a first cell culture module, the second flow path has a second accommodation section for detachably accommodating a second cell culture module, the first cell culture module contains first cells having a barrier function and a first culture gel, and has a light-permeable first window formed from a hydrogel or a porous body, the second cell culture module contains second cells and a second culture gel, and has a light-permeable second window formed from a hydrogel or a porous body, and the first accommodation section allows the first cell culture module to block the third flow path.

Preferably, the fluidic device according to the present invention includes the first cell culture module. Preferably, the first cell culture module includes a three-dimensional frame. Preferably, the first window closes at least one first opening bordered by the three-dimensional frame. This configuration allows for increased strength of the first cell culture module, suppressing deformation of the cell culture module.

Preferably, the first cells or a cellular tissue containing the first cells closes a second opening bordered by the three-dimensional frame. This configuration allows for formation of a barrier model including cells or a cellular tissue having a barrier function in one opening of the three-dimensional frame. Preferably, the first cells or the cellular tissue containing the first cells is in close contact with the three-dimensional frame. This configuration allows for improved barrier performance of the barrier model.

Preferably, the first cell culture module is accommodated in the first accommodation section in such a manner that the first cells or the cellular tissue containing the first cells is opposed to the first flow path. This configuration allows for separation of the first flow path from the inside of the first cell culture module using the barrier model, and allows for formation of a blood-brain barrier model, an intestinal tract model, or the like. This configuration also allows for migration of a test substance that has passed through the barrier model or a humoral factor secreted by the cells in the first cell culture module toward the second flow path.

Preferably, the first accommodation section allows the first cells or the cellular tissue containing the first cells to be exposed to a flow in the first flow path. This configuration allows for improved barrier performance of the barrier model.

Preferably, the first cell culture module has a third window formed from a light-permeable resin. Preferably, the third window closes at least one third opening bordered by the three-dimensional frame. Preferably, the first cell culture module is accommodated in the first accommodation section in such a manner that the third window is opposed to a flow path wall of the third flow path. This configuration allows for improved adhesion between the first culture gel and the third window, keeping the first culture gel from coming off the third window. Furthermore, the light-permeable resin window, which is impermeable to ions, enables an edge of an endothelial cell layer containing endothelial cells to adhere to the window, preventing a leak of the barrier from being formed between the endothelial cell layer and the window.

Preferably, the first cells or the cellular tissue containing the first cells has a filtering function. Preferably, the first cells are any of vascular endothelial cells, intestinal epithelial cells, and epidermal cells. Preferably, the first cell culture module includes a blood-brain barrier model including vascular endothelial cells, pericytes, and astrocytes. Preferably, the hydrogel includes at least one of an agarose gel, a polyacrylamide gel, sodium alginate, or a collagen gel. Preferably, the porous body includes at least one of a porous material sheet, a mesh, an etching sheet, a non-woven fabric, or a woven fabric.

Preferably, the third flow path has substantially the same width as the first cell culture module in the first accommodation section. This configuration allows the first cell culture module to block the third flow path, preventing formation of a gap between a side wall of the third flow path and the first cell culture module. As such, it is possible to separate a side toward the first flow path from a side toward the second flow path in a fluid-tight manner using the barrier model formed in the first cell culture module.

Preferably, the first accommodation section allows the first cell culture module to be located adjacent to the first flow path. This configuration allows the first cells or the cellular tissue containing the first cells to be exposed to a flow in the first flow path, improving the barrier performance of the barrier model.

Preferably, the second accommodation section allows the second cell culture module to be located at a confluence of the second flow path and the third flow path. This configuration can increase the probability that a test substance that has passed through the barrier model in the first cell culture module or a humoral factor secreted by the cells in the first cell culture module reaches the second cells in the second cell culture module.

Preferably, the second flow path has a third accommodation section for detachably accommodating a third cell culture module. Preferably, the third cell culture module contains third cells and a third culture gel, and has a light-permeable fourth window formed from a hydrogel or a porous body. This configuration allows for study of interaction between the second cells and the third cells that is caused by a test substance that has passed through the barrier model in the first cell culture module.

Preferably, the second flow path has a fourth accommodation section for detachably accommodating a humoral factor detection module. This configuration allows for detection of a humoral factor secreted by the cells in the first cell culture module or the cells in the second cell culture module.

The following describes a plurality of embodiments of the present invention with reference to the drawings. Configurations indicated in the drawings and the following descriptions are merely illustrative, and do not limit the scope of the present invention thereto.

First Embodiment

FIG. 1 is a schematic plan view of a fluidic device according to the present embodiment. FIGS. 2(*a*) to 2(*c*) are each a schematic cross-sectional view of the fluidic device. FIG. 3 is a schematic perspective view of a first cell culture module including cells forming a blood-brain barrier model. FIGS. 4 and 5 are each a schematic cross-sectional view of the first cell culture module. FIG. 6 is a schematic perspective view of a second cell culture module including neurons. FIG. 7 is a schematic cross-sectional view of the second cell culture module. FIG. 8 is a schematic plan view of the fluidic device with the first and second cell culture modules attached thereto. FIGS. 9(*a*) to 9(*c*) and 10 are each a schematic cross-sectional view of the fluidic device in this state.

A fluidic device 50 according to the present embodiment is characterized by the following. The fluidic device 50 includes a base 2 and a lid member 3. The base 2 and the lid member 3 are configured to form, between the base 1 and the lid member 3, a first flow path 4, a second flow path 5, and a third flow path 6 through the base 2 and the lid member 3 being bonded to each other. The third flow path 6 connects the first flow path 4 and the second flow path 5. The third flow path 6 has a first accommodation section 7 for detachably accommodating a first cell culture module 11. The second flow path 5 has a second accommodation section 8 for detachably accommodating a second cell culture module 12. The first cell culture module 11 contains first cells 16 having a barrier function and a first culture gel 21, and has a light-permeable first window 26a formed from a hydrogel or a porous body. The second cell culture module 12 contains second cells 17 and a second culture gel 22, and has a light-permeable second window 26a formed from a hydrogel or a porous body. The first accommodation section 7 allows the first cell culture module 11 to block the third flow path 6.

The fluidic device 50 enables culture of cells contained in the first cell culture module 11 and the second cells 17 contained in the second cell culture module 12 by allowing a culture solution to flow through the first flow path 4 or the second flow path 5. The fluidic device 50 may be a fluidic chip, a perfusion culture device, a culture environment control device, or an organ-on-a-chip.

The fluidic device 50 includes the base 2. A groove that servs as the first flow path 4, the second flow path 5, or the third flow path 6 may be formed in the base 2. The base 2 may be formed from a polymer material such as silicone rubber (for example, PDMS), acrylic resin (for example, PMMA), or polycarbonate, or may be formed from glass. The base 2 is preferably formed from a light-permeable material. This configuration allows for observation of the cells being cultured in the first cell culture module 11 or the cells being cultured in the second cell culture module 12.

The fluidic device 50 includes the lid member 3. The lid member 3 is, for example, a glass plate. This configuration allows for observation of the cells in the first cell culture module 11 or the cells in the second cell culture module 12 through the lid member 3. The lid member 3 is bonded to the base 2 when cells are cultured using the fluidic device 50. The base 2 and the lid member 3 may be bonded by using adhesiveness of the base 2. The base 2 and the lid member 3 may alternatively be bonded by pressure welding between the base 2 and the lid member 3 using a clip or the like.

The lid member 3 may be provided to be a flow path wall of the first flow path 4, the second flow path 5, or the third flow path 6. The lid member 3 may also be provided to be peelable or detachable from the base 2. This configuration allows the first cell culture module 11 or the second cell culture module 12 to be detached from the fluidic device 50 after the cells have been cultured using the fluidic device 50, so that the cells in the module can be observed.

The base 2 and the lid member 3 are configured to form, between the base 2 and the lid member 3, the first flow path 4, the second flow path 5, and the third flow path 6, which establishes communication between the first flow path 4 and the second flow path 5, through the base 2 and the lid member 3 being bonded to each other. The first flow path 4, the second flow path 5, or the third flow path 6 may have a structure including a groove in the base 2 and the lid member 3 covering the groove, or may have a structure including a groove in the lid member 3 and the base 2 covering the groove.

The first flow path 4 may have an inlet 31*a* at one end thereof and an outlet 32*a* at another end thereof. This configuration allows a first liquid such as a culture solution to be injected from the inlet 31*a*, to flow through the first flow path 4, and to be discharged from the outlet 32*a*. The first flow path 4 may be provided as a flow path outside a barrier of a barrier model formed in the first cell culture module 11. The second flow path 5 may have an inlet 31*b* at one end thereof and an outlet 32*b* at another end thereof. This configuration allows a second liquid such as a culture solution to be injected from the inlet 31*b*, to flow through the second flow path 5, and to be discharged from the outlet 32*b*. The second flow path 5 has the second accommodation section 8 for detachably accommodating the second cell culture module 12. The second flow path 5 may be provided as a flow path inside the barrier of the barrier model formed in the first cell culture module 11.

The third flow path 6 is provided to establish communication between the first flow path 4 and the second flow path 5. The third flow path 6 has the first accommodation section 7 for detachably accommodating the first cell culture module 11. The first accommodation section 7 is provided in such a manner as to allow the first cell culture module 11 to block the third flow path 6. Preferably, the third flow path 6 has a square cross section.

The first flow path 4, the second flow path 5, the third flow path 6, the first accommodation section 7, and the second accommodation section 8 may be provided, for example, as in the fluidic device 50 illustrated in FIGS. 1 and 2(*a*) to 2(*c*).

FIGS. 8 and 9(*a*) to 9(*c*) show the fluidic device 50 illustrated in FIGS. 1 and 2(*a*) to 2(*c*) with the first cell culture module 11 illustrated in FIGS. 3 and 4 attached to the first accommodation section 7 of the fluidic device 50 and with the second cell culture module 12 illustrated in FIGS. 6 and 7 attached to the second accommodation section 8.

The first cell culture module 11 contains therein the first cells 16 having the barrier function and the first culture gel 21, and has light-permeable windows 26*a* formed from a hydrogel or a porous body. The first cell culture module 11 is detachably accommodated in the first accommodation section 7 provided in the third flow path 6. The first cell culture module 11 may have a light-permeable window 26*b* formed from a light-permeable resin. Examples of light-permeable resins include silicone rubber, polypropylene, and polyethylene.

The first cell culture module 11 may include a three-dimensional frame (space frame) 25. The three-dimensional frame 25 is a member that supports the structure of the first cell culture module 11 and is a framework structure of the first cell culture module 11. The three-dimensional frame 25 may be polyhedral, square, or cylindrical in shape. The three-dimensional frame 25 is preferably a cube or a cuboid. In a configuration in which the three-dimensional frame 25 is polyhedral in shape, for example, the three-dimensional frame 25 has a straight frame piece at an edge between every two adjacent faces. The three-dimensional frame 25 has openings, which are the faces of the polyhedron that are bordered by the straight frame pieces.

The openings of the three-dimensional frame 25 are closed by the windows 26*a* so that the first cell culture module 11 can contain the cells and the first culture gel 21. However, the opening located at the top of the three-dimensional frame 25 does not have to be closed by the window 26*a*. At least one of the plurality of windows 26*a* of the first cell culture module 11 may be removed before the first cell culture module 11 is attached to the first accommodation section 7.

For example, the three-dimensional frame 25 included in the first cell culture module 11 illustrated in FIGS. 3 and 4 is a cube and has an opening on each face thereof. The openings on the bottom face and the side faces of the three-dimensional frame 25 are closed by the windows 26*a*. The cells and the first culture gel 21 are contained in a space surrounded by these windows 26*a*.

In a configuration in which the first cell culture module 11 has light-permeable windows 26*b* formed from silicone rubber, the first cell culture module 11 may have a cross section as shown in FIG. 5. Such light-permeable silicone rubber is, for example, PDMS. In this case, the opening on the bottom face of the three-dimensional frame 25 is closed by the light-permeable window 26*a* formed from a hydrogel or a porous body, and the openings on the side faces of the three-dimensional frame 25 are closed by the light-permeable windows 26*b* formed from silicone rubber.

The three-dimensional frame 25 may be formed from a biocompatible resin. The three-dimensional frame 25 may be formed from, for example, polycarbonate.

The windows 26*a* are formed from a hydrogel or a porous body and constitute the bottom and side walls of the first cell culture module 11. In a configuration in which the first cell culture module 11 has the windows 26*b*, the window 26*a* constitutes the bottom of the first cell culture module 11. The hydrogel and the porous body are permeable to nutrients, a test substance, a humoral factor, or the like. This permeability allows nutrients contained in the culture solution flowing through the first flow path 4 or the second flow path 5 to be supplied to the cells being cultured in the first cell culture module 11. This permeability also allows the test substance or the humoral factor to move from the first cell culture module 11 to the second cell culture module 12.

The windows 26*a* and 26*b* are light-permeable, and allow the first cells 16 being cultured in the first cell culture module 11 to be observed therethrough.

No particular limitations are placed on the hydrogel that forms the windows 26*a* as long as the hydrogel permits proteins to pass therethrough and has enough hardness to be capable of self-support. The hydrogel is a network formed from linking dispersoid in water and is in the form of a solid as a whole system. The windows 26*a* may have, for example, a gel strength of 50 g/cm$^2$ or higher and 10000 g/cm$^2$ or lower. This configuration keeps the windows 26*a* from being deformed by the weight of the first culture gel 21 in the first cell culture module 11. This configuration also enables the windows 26a to be protein-permeable. The gel strength can be adjusted by adjusting the concentration of the dispersoid forming the network. An overly low concentration of the dispersoid leads to a decrease in the gel strength. An overly high concentration of the dispersoid leads to a decrease in the protein permeability. Note that an appropriate concentration of the dispersoid varies depending on the type of the dispersoid.

The hydrogel that forms the windows 26a may include, for example, an agarose gel, a polyacrylamide gel, sodium alginate, or a collagen gel. This configuration enables the windows 26a to be light-permeable. This configuration also allows nutrients such as proteins contained in the culture solution flowing through the first flow path 4 or the second flow path 5 to permeate through the windows 26a, so that the nutrients can be supplied to the first culture gel 21 and the cells. In the case of the windows 26a being an agarose gel, the agarose gel may have, for example, an agarose concentration of 0.5% to 4.0%. In the case of the windows 26a being a polyacrylamide gel, the polyacrylamide gel may have, for example, a polyacrylamide concentration of 3% to 20%. In the case of the windows 26a containing sodium alginate, the windows 26a can be formed by adding calcium ions to an aqueous sodium alginate solution, and thus causing gelation thereof. In the case of the windows 26a being a collagen gel, the windows 26a can be formed from a high concentration of collagen gel. This configuration enables the windows 26a to have a sufficient strength.

The porous body that forms the windows 26a is a member having a large number of micropores. Examples of the porous body include a porous material sheet, a mesh, an etching sheet, a non-woven fabric, and a woven fabric. The porous body may have a sheet shape. Preferably, the porous body has biocompatibility. The porous body may alternatively be formed from a resin such as polycarbonate, may be formed from a metal such as gold, or may be formed from an inorganic compound such as glass. In the case of the windows 26a formed from a porous body, the windows 26a can be formed by bonding a porous body sheet to the three-dimensional frame 25.

The first culture gel 21 is contained in the first cell culture module 11 and serves as a scaffold for three-dimensional culture of the cells. The first culture gel 21 may contain nutrients for the three-dimensional culture of the cells. The nutrients are consumed by the cells. The nutrients are supplied from the culture solution outside the first culture gel 21 through the windows 26a. As such, it is possible to continuously supply the nutrients to the cells.

The first culture gel 21 may contain, for example, any of collagen, laminin, entactin, and proteoglycan. The first culture gel 21 may also contain, for example, any of a TGF-β, a fibroblast growth factor, and a tissue plasminogen activator. Matrigel (registered trademark), for example, may be used as the first culture gel 21.

The first cells 16 refer to cells that have the barrier function and that are cultured in the first culture gel 21 in the first cell culture module 11. The first cells 16 may be cells contained in a cellular tissue having the barrier function. The first cells 16 may be cells that have a selective uptake mechanism (filtering function) or cells contained in a cellular tissue having a selective uptake function (filtering function).

Examples of the cells or the cellular tissue (first cells 16) having the barrier function include vascular endothelial cells, intestinal epithelial cells, epidermal cells, nasal epithelial cells, and bronchial epithelial cells. Examples of the cells or the cellular tissue (first cells 16) having the barrier function and the filtering function include vascular endothelial cells in a blood-brain barrier, vascular endothelial cells in a vascular-retinal barrier, tubular cells in a kidney, and intestinal epithelial cells in an intestine.

The cells or the cellular tissue (first cells 16) having the barrier function or the filtering function may be provided so as to close an opening bordered by the three-dimensional frame 25 and may be in close contact with the three-dimensional frame 25.

In a configuration in which one type of cells (first cells 16) having the barrier function close the opening bordered by the three-dimensional frame 25, these cells are in close contact with the frame bordering the opening.

In a configuration in which the cellular tissue (containing the first cells 16) having the barrier function closes the opening bordered by the three-dimensional frame 25, cells forming the cellular tissue are bound to their neighboring cells through tight junctions. Furthermore, this cellular tissue is in close contact with the three-dimensional frame 25 at the periphery of the cellular tissue.

Such a configuration allows for formation of a barrier model of, for example, vascular endothelium, an intestinal tract, or epidermis having the barrier function on one face of the first cell culture module 11.

For example, a blood-brain barrier model is formed in the first cell culture module 11 illustrated in FIG. 3, 4, or 5. This blood-brain barrier model includes cerebrovascular endothelial cells 35 (first cells 16), pericytes 36, and astrocytes 37. A cellular tissue containing the plurality of cerebrovascular endothelial cells 35 (first cells 16) is cultured on the top face of the first cell culture module 11 using the first culture gel 21 as a scaffold, and the cellular tissue closes the opening on the top face of the three-dimensional frame 25. The cellular tissue is in close contact with the three-dimensional frame 25 at the periphery of the cellular tissue. The cerebrovascular endothelial cells 35 play a central role in the blood-brain barrier.

Furthermore, the pericytes 36 and astrocytes 37 are cultured in the first culture gel 21 in the first cell culture module 11. These cells are closely involved in the barrier function and the filtering function of the blood-brain barrier.

The first cell culture module 11 illustrated in FIGS. 3 and 4 can be formed as described below.

First, a cubic three-dimensional frame 25 having an opening on each of six faces thereof is prepared, and a sol for forming windows is poured into the openings of the three-dimensional frame 25 and gelled to form film-shaped or sheet-shaped hydrogel windows 26a. The windows 26a are respectively formed on five faces of the three-dimensional frame 25 as described above. Thereafter, an un-gelled first culture gel 21 and the astrocytes 37 are injected into a cubic space within the three-dimensional frame 25, and then the culture gel is gelled. Thereafter, the un-gelled first culture gel 21 and the pericytes 36 are poured into the cubic space within the three-dimensional frame 25, and then the first culture gel 21 is gelled. At this stage, the volume of the injection is adjusted so that the top surface of the first culture gel 21 is located slightly below the top face of the three-dimensional frame 25. Thereafter, the top surface of the first culture gel 21 is seeded with the cerebrovascular endothelial cells 35. The thus produced first cell culture module 11 is immersed in the culture solution, so that the cerebrovascular endothelial cells 35, the pericytes 36, and the astrocytes are three-dimensionally cultured. Through the above, the first cell culture module 11 illustrated in FIGS. 3 and 4 can be produced.

In the case of the first cell culture module 11 illustrated in FIG. 5, the hydrogel window 26a is formed in the opening at the bottom of the three-dimensional frame 25, and silicone rubber windows 26b are formed on the side faces (four faces) of the three-dimensional frame 25. The windows 26b can be formed, for example, by pouring liquid PDMS into the openings of the three-dimensional frame 25 and curing the PDMS.

The first accommodation section 7 of the fluidic device 50 is a part for detachably accommodating the first cell culture module 11. The first cell culture module 11 blocks the third flow path 6 when the first cell culture module 11 is in place in the first accommodation section 7. The third flow path 6 may have, for example, substantially the same width and substantially the same height as the first cell culture module 11 in the first accommodation section 7. This configuration allows the first cell culture module 11 in place in the first accommodation section 7 to block the third flow path 6.

The first accommodation section 7 may accommodate the first cell culture module 11 in such a manner that the face provided with the window 26a is opposed to the second flow path 5 and the face provided with the cells or the cellular tissue (first cells 16) having the barrier function or the filtering function is opposed to the first flow path 4. The first cell culture module 11 may be, for example, accommodated in the first accommodation section 7 as in the fluidic device 50 illustrated in FIGS. 8 to 10. The window 26a opposed to the second flow path 5 may be removed from the three-dimensional frame 25 before the first cell culture module 11 is attached to the first accommodation section 7. This configuration allows migratory cells in the first cell culture module 11 to migrate to the second cell culture module 12 or allows migratory cells in the second cell culture module 12 to migrate to the first cell culture module 11.

In the case of the first cell culture module 11 having the silicone rubber windows 26b, the first cell culture module 11 is accommodated in the first accommodation section 7 in such a manner that the windows 26b are opposed to the flow path wall of the third flow path 6.

When the first cell culture module 11 is in place in the first accommodation section 7, no liquid such as the culture solution flows into the first culture gel 21 from the faces of the first cell culture module 11 that are opposed to a bottom surface, opposite side surfaces, and a ceiling surface of the first accommodation section 7 (third flow path 6). If these faces have the hydrogel windows 26a, therefore, a portion of the first culture gel 21 that is adjacent to any of the windows 26a can shrink, letting the first culture gel 21 come off the window 26a.

Providing the faces of the first cell culture module 11 that are opposed to the bottom surface, the opposite side surfaces, and the ceiling surface of the first accommodation section 7 (third flow path 6) with the silicone rubber windows 26b improves adhesion between the first culture gel 21 and the windows 26b, keeping the first culture gel 21 from coming off any of the windows. Furthermore, the silicone rubber windows, which are impermeable to ions, enable edges of an endothelial cell layer containing endothelial cells to adhere to the windows, preventing a leak of the barrier from being formed between the endothelial cell layer and any of the windows.

Since the face of the first cell culture module 11 that is provided with the cells or the cellular tissue (first cells 16) having the barrier function has the barrier model of, for example, vascular endothelium, an intestinal tract, or epidermis having the barrier function, it is possible to separate a side toward the first flow path 4 from a side toward the second flow path 5 using this barrier model. Furthermore, since the third flow path 6 is blocked by the first cell culture module 11, it is possible to prevent formation of a gap between the inner wall of the third flow path 6 and the first cell culture module 11. Furthermore, since the cells or the cellular tissue (first cells 16) having the barrier function in the first cell culture module 11 is in close contact with the three-dimensional frame 25, it is possible to prevent formation of a gap between the three-dimensional frame 25 and the cells or the cellular tissue (first cells 16) having the barrier function. It is therefore possible to keep a substance contained in the liquid flowing through the first flow path 4 from flowing into the second flow path 5 without going through the cells or the cellular tissue (first cells 16) having the barrier function, allowing for formation of a biological environment model in which the first flow path 4 is equivalent to the outside of the barrier and the second flow path 5 is equivalent to the inside of the barrier.

In a case where a blood-brain barrier model such as shown in FIGS. 3 and 4 is formed in the first cell culture module 11, and this first cell culture module 11 is attached to the first accommodation section 7 as shown in FIG. 10, for example, the first flow path 4 is equivalent to a blood vessel and the second flow path 5 is equivalent to a central nervous system side. For another example, in a case where a tubule model is formed in the first cell culture module 11, the first flow path 4 is equivalent to a tubule through which primary urine flows, and the second flow path 5 is equivalent to a blood vessel. For another example, in a case where an intestinal tract model is formed in the first cell culture module 11, the first flow path 4 is equivalent to an intestinal tract (digestive tract), and the second flow path 5 is equivalent to a blood vessel. For another example, in a case where an epidermis model is formed in the first cell culture module 11, the first flow path 4 is equivalent to the outside of a body, and the second flow path 5 is equivalent to the inside of the body.

Preferably, the first accommodation section 7 is provided in such a manner as to allow the first cell culture module 11 to be located adjacent to the first flow path 4. As a result of such a first accommodation section 7 receiving the first cell culture module 11 attached thereto, the cells or the cellular tissue (first cells 16) having the barrier function in the first cell culture module 11 can be exposed to the flow in the first flow path 4. This configuration allows for appropriate evaluation of the barrier function of the cells or the cellular tissue (first cells 16). This configuration also allows for reinforced tight junctions in the cellular tissue.

The second accommodation section 8 of the fluidic device 50 is a part for detachably accommodating the second cell culture module 12. The second accommodation section 8 is provided in the second flow path 5. Nutrients can be supplied to the second cells 17 being cultured in the second cell culture module 12 by attaching the second cell culture module 12 to the second accommodation section 8 and causing the culture solution to flow through the second flow path 5.

The second accommodation section 8 may be provided in such a manner as to allow the second cell culture module 12 to be located at a confluence of the second flow path 5 and the third flow path 6. This configuration makes it easier for a test substance that has passed through the barrier model in the first cell culture module 11 to enter the second cell culture module 12 and makes it easier to study an effect of the test substance on the second cells 17.

The second accommodation section 8 may be provided in such a manner as to allow the second cell culture module 12 to block the third flow path 6. Furthermore, the second accommodation section 8 may be provided in such a manner as to allow the second cell culture module 12 to be located adjacent to the first cell culture module. This configuration makes it easier for a test substance that has passed through the barrier model in the first cell culture module 11 to enter the second cell culture module 12 and makes it easier to study an effect of the test substance on the second cells 17.

The second cell culture module 12 contains the second cells 17 and the second culture gel 22, and has the light-permeable windows 26a formed from a hydrogel or a porous body. The second cell culture module 12 may have a three-dimensional frame 25.

The configuration and the production method of the second cell culture module 12 are substantially the same as the configuration and the production method of the first cell culture module 11. However, the second cells 17 that are cultured in the second cell culture module 12 may be of different type from the cells that are cultured in the first cell culture module 11.

The description of the three-dimensional frame 25 of the first cell culture module 11 given above is applicable to the three-dimensional frame 25 of the second cell culture module 12. The description of the windows 26a of the first cell culture module 11 given above is applicable to the windows 26a of the second cell culture module 12. The description of the first culture gel 21 in the first cell culture module 11 given above is applicable to the second culture gel 22 in the second cell culture module 12.

In the first cell culture module 11, the cellular tissue containing the first cells 16 having the barrier function is cultured in the opening on one face of the three-dimensional frame 25. In the second cell culture module 12, by contrast, the openings on all faces of the three-dimensional frame 25 may be provided with the windows 26a. At least one of the windows 26a may be removed from the three-dimensional frame 25 before the second cell culture module 12 is incorporated into the fluidic device 50.

The second cells 17 that are cultured in the second cell culture module 12 may be cells or a cellular tissue inside the barrier of the barrier model formed in the first cell culture module 11. In a case where a blood-brain barrier model or a blood-retinal barrier model is formed in the first cell culture module 11, for example, the second cells 17 may be neurons. For example, as shown in FIGS. 6 and 7, the second cell culture module 12 may include neurons 38 three-dimensionally cultured using the second culture gel 22 as a scaffold.

For another example, in a case where an intestinal tract model is formed in the first cell culture module 11, the second cells 17 may be hepatocytes. For another example, in a case where an epidermis model is formed in the first cell culture module 11, the second cells 17 may be cells contained in a subcutaneous tissue.

By attaching the second cell culture module 12 such as described above to the second accommodation section 8, it is possible to study an effect, on the second cells 17, of a test substance that has passed through the barrier model formed in the first cell culture module 11. It is also possible to study an effect, on the second cells 17, of a humoral factor secreted by the cells in the first cell culture module 11 due to the effect of the test substance. This will be explained below.

First, the first cell culture module 11 having a barrier model (first cells 16) is attached to the first accommodation section 7 of the fluidic device 50. At this stage, the second cell culture module 12 is not attached to the second accommodation section 8. In the fluidic device 50 in this state, the first liquid containing the test substance is caused to flow through the first flow path 4, and the second liquid is caused to flow through the second flow path 5. If the test substance is able to pass through the barrier model, the test substance passes through the first cell culture module 11, flows into the second flow path 5, and is discharged from the outlet 32b of the second flow path 5. If the test substance is not able to pass through the barrier model, the test substance flows through the first flow path 4 and is discharged from the outlet 32a of the first flow path 4 without entering the first cell culture module 11. Thus, it is possible to determine whether or not the test substance passes through the barrier model by analyzing whether or not the test substance is detected in the second liquid discharged from the outlet 32b of the second flow path 5.

Next, the second cell culture module 12 including the second cells 17 is attached to the second accommodation section 8 of the fluidic device 50. Then, the first liquid containing the test substance, which has been confirmed to be able to pass through the barrier model, is caused to flow through the first flow path 4, and the second liquid is caused to flow through the second flow path 5. The test substance contained in the first liquid flowing through the first flow path 4 passes through the barrier model in the first cell culture module 11 and enters the second cell culture module 12 through the second liquid or directly. If the test substance affects the second cells 17 in the second cell culture module 12, a change occurs in, for example, shape, state, or growth of the second cells 17. If the test substance affects the cells in the first cell culture module 11, a change occurs in, for example, shape, state, or growth of the cells. If the cells in the first cell culture module 11 secrete a humoral factor due to an effect of the test substance, this humoral factor can affect the second cells 17.

In a case where the first liquid containing a test substance A that is able to pass through the barrier model and a test substance B that is not able to pass through the barrier model is caused to flow through the first flow path 4, for example, the test substance B is not able to enter the first cell culture module 11 and flows through the first flow path 4 as shown in FIG. 10. The test substance A enters the first cell culture module 11 from the first flow path 4 and further enters the second cell culture module 12. The test substance A can then affect the second cells 17.

Next, the first cell culture module 11 or the second cell culture module 12 is detached from the fluidic device 50 and set in a microscope. The cells in the first cell culture module 11 or the cells in the second cell culture module 12 are observed three-dimensionally. In a case where the first cell culture module 11 has a configuration such as shown in FIGS. 3 and 4, and the second cell culture module 12 has a configuration such as shown in FIGS. 6 and 7, for example, the three-dimensional shapes of the cerebrovascular endothelial cells 35, the pericytes 36, and the astrocytes 37 can be grasped by observing these cells through each face of the first cell culture module 11. Likewise, the three-dimensional shape of the neurons 38 can be grasped by observing the neurons 38 through each face of the second cell culture module 12. As such, it is possible to study how the test substance having passed through the barrier model has affected the cells in the first cell culture module 11 or the cells in the second cell culture module 12.

Second Embodiment

FIGS. 11 and 12 are each a schematic cross-sectional view of a fluidic device 50 according to the present embodiment. FIG. 11 shows the fluidic device 50 without first and second cell culture modules attached thereto. FIG. 12 shows the fluidic device 50 with the first and second cell culture modules attached thereto.

The fluidic device 50 shown in FIG. 11 has a single first flow path 4, and a second flow path 5a and a second flow path 5b respectively provided at opposite sides of the single first flow path 4. The fluidic device 50 also has a third flow path 6a establishing communication between the first flow path 4 and the second flow path 5a, and a third flow path 6b establishing communication between the first flow path 4 and the second flow path 5b. The third flow path 6a has a first accommodation section 7a. The third flow path 6b has a first accommodation section 7b. The second flow path 5a has a second accommodation section 8a. The second flow path 5b has a second accommodation section 8b.

In the fluidic device 50 shown in FIG. 12, first cell culture modules 11a and 11b are respectively attached to the first accommodation sections 7a and 7b, and second cell culture modules 12a and 12b are respectively attached to the second accommodation sections 8a and 8b.

For example, the first cell culture modules 11a and 11b each having a blood-brain barrier model (including first cells 16) may be respectively attached to the first accommodation sections 7a and 7b, the second cell culture module 12a including normal neurons (second cells 17) may be attached to the second accommodation section 8a, and the second cell culture module 12b including disease-derived neurons (second cells 17) generated from iPS cells derived from a patient with a refractory disease such as Alzheimer's disease or Parkinson's disease may be attached to the second accommodation section 8b. Then, a test substance that is able to pass through the blood-brain barrier models in the first cell culture modules 11a and 11b is caused to flow through the first flow path 4, so that the test substance can pass through the blood-brain barrier models in the first cell culture modules 11a and 11b, and affect the normal neurons in the second cell culture module 12a and the disease-derived neurons in the second cell culture module 12b. Thereafter, the second cell culture modules 12a and 12b are detached from the fluidic device 50, and the normal neurons and the disease-derived neurons are three-dimensionally observed to compare shape, state, growth, and the like therebetween. Thus, the effect of the test substance on the disease-derived neurons can be studied more closely.

In the first embodiment, the first cell culture module 11 and the second cell culture module 12 are cubic in shape. In the present embodiment, by contrast, the first cell culture modules 11a and 11b, and the second cell culture modules 12a and 12b are cuboid in shape. Furthermore, cells or a cellular tissue (first cells 16) having the barrier function is cultured so as to close the opening of the wider face of the first cell culture module 11. According to this configuration, it is possible to increase the area of contact between the first liquid flowing through the first flow path 4 and the cells or the cellular tissue (first cells 16) having the barrier function, it is possible to increase the amount of the test substance that is able to pass through the barrier models to reach the second cells 17, and thus it is possible to increase the effect of the test substance on the second cells 17.

Other than the foregoing, the second embodiment has the same configuration as the first embodiment. The description of the first embodiment also applies to the second embodiment unless contradicted by context.

Third Embodiment

FIGS. 13(*a*) to 13(*c*) are each a schematic cross-sectional view of a fluidic device according to the present embodiment. FIG. 13(*a*) shows the fluidic device without first, second, and third cell culture modules attached thereto. FIGS. 13(*b*) and 13(*c*) show the fluidic device with the first, second and third cell culture modules attached thereto.

A fluidic device 50 according to the present embodiment has a third accommodation section 9 for detachably accommodating a third cell culture module 13 in addition to a first accommodation section 7 and a second accommodation section 8. The third accommodation section 9 is provided in a second flow path 5. The third accommodation section 9 may be located upstream or downstream of the second accommodation section 8. Preferably, the third accommodation section 9 is located downstream of the second accommodation section 8.

The third cell culture module 13 contains third cells 18 and a third culture gel 23, and has light-permeable windows 26a formed from a hydrogel or a porous body. The third cell culture module 13 may have a three-dimensional frame 25.

The configuration and the production method of the third cell culture module 13 are substantially the same as the configuration and the production method of the first cell culture module 11 or the second cell culture module 12. However, the third cells 18 that are cultured in the third cell culture module 13 may be of different type from the cells that are cultured in the first cell culture module 11 or the cells that are cultured in the second cell culture module 12.

The description of the three-dimensional frame 25 of the first cell culture module 11 given above is applicable to the three-dimensional frame 25 of the third cell culture module 13. The description of the windows 26a of the first cell culture module 11 given above is applicable to the windows 26a of the third cell culture module 13. The description of the first culture gel 21 in the first cell culture module 11 given above is applicable to the third culture gel 23 in the third cell culture module 13.

In the first cell culture module 11, the cellular tissue containing the first cells 16 having the barrier function is cultured in the opening on one face of the three-dimensional frame 25. In the third cell culture module 13, by contrast, the openings on all faces of the three-dimensional frame 25 may be provided with the windows 26a. At least one of the windows 26a may be removed from the three-dimensional frame 25 before the third cell culture module 13 is incorporated into the fluidic device 50. This configuration allows migratory cells in the second cell culture module 12 to migrate to the third cell culture module 13 or allows migratory cells in the third cell culture module 13 to migrate to the second cell culture module 12.

The third cells 18 that are cultured in the third cell culture module 13 may be those that are affected by, for example, a humoral factor produced by the second cells 17 in the second cell culture module 12 or a metabolite formed by the second cells 17. The humoral factor refers to an intercellular messenger that transmits information through a body fluid such as blood, and examples thereof include hormones, cytokines, and exosomes.

In the fluidic device 50 shown in FIG. 13(*b*), for example, the first cell culture module 11 has a blood-brain barrier model (including first cells 16), the second cell culture module 12 includes neurons 38 (second cells 17), and the third cell culture module 13 includes immune cells 39 (third cells 18) such as white blood cells. In this fluidic device 50, a biological environment model is formed in which the first flow path 4 is equivalent to a blood vessel and the second flow path 5 is equivalent to the inside of a brain. In a case where the first liquid containing a test substance that is able to pass through the blood-brain barrier model is caused to flow through the first flow path 4 in this fluidic device 50, the test substance passes through the blood-brain barrier and reaches the neurons 38 in the second cell culture module 12. The neurons 38 affected by the test substance secrete a humoral factor, and the humoral factor reaches the immune cells 39 in the third cell culture module 13 along with the second liquid. The immune cells 39 affected by the humoral factor start to migrate toward, for example, the neurons 38.

Whether or not the immune cells 39 have started to migrate can be confirmed by detaching the third cell culture module 13 from the fluidic device 50, three-dimensionally observing the immune cells 39 therein, and comparing a result of the three-dimensional observation against a result of an observation of the immune cells 39 performed before the experiment.

For example, in the fluidic device 50 shown in FIG. 13(c), the first cell culture module 11 includes intestinal epithelial cells 40 (first cells 16), the second cell culture module 12 includes hepatocytes 41 (second cells 17), and the third cell culture module 13 includes renal cells 42 (third cell 18). In this fluidic device 50, a biological environment model is formed in which the first flow path 4 is equivalent to an intestinal tract and the second flow path 5 is equivalent to a liver or a kidney. In a case where the first liquid containing a test substance that is able to pass through the intestinal epithelial cells 40 is caused to flow through the first flow path 4 in this fluidic device 50, the test substance passes through the intestinal epithelial cells 40 and reaches the hepatocytes 41 in the second cell culture module 12. The test substance is metabolized by the hepatocytes 41, and the resulting metabolite reaches the renal cells 42 in the third cell culture module 13 along with the second liquid and affects the renal cells 42.

How the renal cells 42 have been affected can be found out by detaching the third cell culture module 13 from the fluidic device 50, three-dimensionally observing the renal cells 42 therein, and comparing a result of the three-dimensional observation against a result of an observation of the renal cells 42 performed before the experiment.

As described above, the use of the fluidic device 50 according to the present embodiment allows for formation of a biological environment model reproducing the inside and the outside of a barrier of a biological tissue having the barrier function. Furthermore, the use of the fluidic device 50 according to the present embodiment allows for study of an effect, on the second cells 17 inside the barrier, of the test substance that has passed through the barrier model, and study of interaction between the second cells 17 and the third cells 18.

Other than the foregoing, the third embodiment has the same configuration as the first or second embodiment. The description of the first or second embodiment also applies to the third embodiment unless contradicted by context.

Fourth Embodiment

FIGS. 14(a) and 14(b) are each a schematic cross-sectional view of a fluidic device according to the present embodiment. FIG. 14(a) shows the fluidic device without first and second cell culture modules and a humoral factor detection module attached thereto. FIG. 14(b) shows the fluidic device with the first and second cell culture modules and the humoral factor detection module attached thereto.

A fluidic device 50 according to the present embodiment has a fourth accommodation section 10 for detachably accommodating a humoral factor detection module 15 in addition to a first accommodation section 7 and a second accommodation section 8. The fourth accommodation section 10 is provided in a second flow path 5. The fourth accommodation section 10 may be located upstream or downstream of the second accommodation section 8. Preferably, the fourth accommodation section 10 is located downstream of the second accommodation section 8.

The humoral factor detection module 15 is for use in detecting a humoral factor secreted from second cells 17 that are cultured in the second cell culture module 12 or a humoral factor secreted from cells that are cultured in the first cell culture module 11. The humoral factor detection module 15 includes a substance that specifically binds to such a humoral factor. Examples of such substances include antibodies, antigens, specific peptides, and nucleic acid aptamers. The module 15 may include beads 44 or a membrane coated with any of these substances. These substances may be those that are capable of specifically binding to the humoral factor secreted by the cells that are cultured in the first cell culture module 11 or the humoral factor secreted by the second cells 17. This configuration makes it possible to capture the humoral factor in the module 15.

After the humoral factor has been captured in the module 15, the module 15 may be detached from the fluidic device 50 for analysis, so that the captured humoral factor can be detected. Examples of analysis methods include enzyme-linked immunosorbent assay (ELISA).

As described above, the use of the fluidic device 50 according to the present embodiment allows for formation of a biological environment model reproducing the inside and the outside of a barrier of a biological tissue having the barrier function. Furthermore, the use of the fluidic device 50 according to the present embodiment allows for detection of a humoral factor secreted by cells inside a barrier that have been affected by a test substance that has passed through the barrier model.

Other than the foregoing, the fourth embodiment has the same configuration as the first to third embodiments. The description of the first to third embodiments also applies to the fourth embodiment unless contradicted by context.

Fluidic Device Production Experiment

A fluidic device such as shown in FIGS. 1, 2(a) to 2(c), 8, and 9(a) to 9(c) was produced. PDMS was used as a material of the base. A glass plate was used for the lid member. FIG. 15(a) shows an image of the fluidic device produced.

Another fluidic device such as shown in FIGS. 11 and 12 was produced. PDMS was used as a material of the base. A glass plate was used for the lid member. FIG. 15(b) shows an image of the fluidic device produced.

Cell Culture Module Production Experiment 1

A cell culture module having a blood-brain barrier model such as shown in FIGS. 3 and 4 was produced.

A cubic polycarbonate three-dimensional frame having a side length of 3 mm was prepared, and a 1.5% agarose gel was poured into an opening of the three-dimensional frame and gelled to form a film-shaped window from the resulting hydrogel. The window was formed on each of five faces of the three-dimensional frame as described above. Thereafter, a collagen gel being an un-gelled culture gel and normal human astrocytes were injected into a cubic space within the three-dimensional frame, and the culture gel was gelled. Thereafter, an un-gelled collagen gel and normal human pericytes were injected into the cubic space within the three-dimensional frame, and the collagen gel was gelled. At this stage, the volume of the injection was adjusted so that the top surface of the collagen gel was located slightly below the top face of the three-dimensional frame. Thereafter, fibronectin was dropped onto the top surface of the collagen gel to improve cell adhesiveness, and then seeding with human cerebrovascular endothelial cells were performed thereon. The thus produced cell culture module was immersed in a culture solution, so that the pericytes and the astrocytes were three-dimensionally cultured in layers in the collagen gel, and the cerebrovascular endothelial cells were planarly cultured on the top surface of the collagen gel. Thereafter, these cells were subjected to staining, the cell culture module was set in a microscope, and the cells were fluorescently imaged. FIG. 16 shows the thus captured image.

A blood-brain barrier (BBB) model was successfully produced by co-culturing the cerebrovascular endothelial cells, the pericytes, and the astrocytes in the cell culture module as described above.

FIG. 17(*a*) is an image of an interface between the collagen gel and one of the windows of the cell culture module (window (hydrogel) located adjacent to the flow path wall of the third flow path during the culture) after 5 days of cell culture in the fluidic device shown in the image in FIG. 15(*a*).

As shown in the image in FIG. 17(*a*), the collagen gel shrank, and a gap was observed between the window and the collagen gel.

Cell Culture Module Production Experiment 2

A cell culture module having a blood-brain barrier model such as shown in FIG. 5 was produced. This cell culture module was produced in the same manner as in "Cell Culture Module Production Experiment 1" except that silicone rubber windows were formed on four side faces of the three-dimensional frame, and a culture gel obtained by mixing Matrigel (registered trademark) and collagen at 1:1 was used instead of the collagen gel. The silicone rubber windows were formed by pouring liquid PDMS into openings of the three-dimensional frame and curing the PDMS.

FIG. 17(*b*) is an image of an interface between the culture gel and one of the windows of the cell culture module (window (silicone rubber) located adjacent to the flow path wall of the third flow path during the culture) after 5 days of cell culture in the fluidic device shown in the image in FIG. 15(*a*).

As shown in the image in FIG. 17(*b*), it was observed that the culture gel had firmly adhered to the window. It is thought that no gap was formed because of the firm adhesion between the silicone rubber window and the culture gel. As a result, formation of a gap between the window and the culture gel was successfully suppressed, and thus deterioration of the barrier function of the blood-brain barrier model was successfully prevented.

Cell Culture and Observation Experiment

The cell culture module produced in "Cell Culture Module Production Experiment 2" was immersed in a culture solution, so that the pericytes and the astrocytes were three-dimensionally cultured in layers in the culture gel, and the cerebrovascular endothelial cells were planarly cultured on the top surface of the culture gel. Thereafter, these cells were subjected to staining, the cell culture module was set in a microscope, and the cells were fluorescently imaged. As the staining, immunostaining of platelet endothelial cell adhesion molecule-1 (CD31), which is an endothelial cell surface marker, PDGF receptor (PDGFRb), which is a pericyte (vascular pericyte) marker, and glial fibrillary acidic protein (GFAP), which is an astrocyte marker, was performed.

FIG. 18 is a fluorescence image of the cell culture module after 2 days of cell culture that was captured from the side (X direction in FIG. 3). FIG. 19 is a fluorescence image of the cell culture module after 5 days of cell culture that was captured from the side (X direction in FIG. 3). FIG. 20 is an image of the cell culture module after 5 days of cell culture that was captured from above (Y direction in FIG. 3). Areas in upper portions of the images in FIGS. 18 and 19 where CD31 (endothelial cells) was observed are the top surface of the culture gel seeded with the human cerebrovascular endothelial cells. CD31 is observed as a reticular pattern, PDGFRb is observed as a granular pattern, and GFAP is observed as a fibrous pattern.

It is apparent from comparison between the image in FIG. 18, which was captured after 2 days of cell culture, and the images in FIGS. 19 and 20, which were captured after 5 days of cell culture, that elongation of the pericytes and the astrocytes is greater in FIGS. 19 and 20. This result confirmed steady culture of the endothelial cells, the pericytes, and the astrocytes. Furthermore, the images shown in FIGS. 19 and 20 confirmed that the top surface of the culture gel was covered with an endothelial cell layer containing the endothelial cells, because CD31 was observed as a reticular pattern on the top surface of the culture gel. The images shown in FIGS. 19 and 20 also confirmed that even the slow-growing astrocytes elongated no less than 200 μm in the culture gel.

Transporter Expression Confirmation Experiment

Endothelial cells, pericytes, and astrocytes in a cell culture module were cultured for 5 days in the same manner as in "Cell Culture and Observation Experiment". Thereafter, these cells were subjected to staining, the cell culture module was set in a microscope, and the cells were fluorescently imaged. As the staining, immunostaining of Glut 1, BCRP, PGP, MRP, or MCT, which are known as key transporters for the blood-brain barrier (BBB), was performed.

FIGS. 21(*a*) to 21(*e*) are each an image of the cell culture module that was captured from above (Y direction in FIG. 3). FIG. 21(*a*) is a fluorescence image of Glut 1. FIG. 21(*b*) is a fluorescence image of BCRP. FIG. 21(*c*) is a fluorescence image of PGP. FIG. 21(*d*) is a fluorescence image of MRP. FIG. 21(*e*) is a fluorescence image of MCT. White portions of these images are fluorescent moieties, indicating transporters.

As seen in these images, expression of Glut 1, BCRP, PGP, MRP, or MCT was confirmed in the cell culture module after 5 days of cell culture.

Tight Junction Confirmation Experiment

Endothelial cells, pericytes, and astrocytes in a cell culture module were cultured for 2 days or for 5 days in the same manner as in "Cell Culture and Observation Experiment". Thereafter, these cells were subjected to staining, the cell culture module was set in a microscope, and the cells were fluorescently imaged. As the staining, immunostaining of ZO-1, which is a tight junction marker, was performed.

FIG. 22(*a*) is a fluorescence image of the cell culture module after 2 days of cell culture that was captured from above (Y direction in FIG. 3). FIG. 22(*b*) is a fluorescence image of the cell culture module after 5 days of cell culture that was captured from above (Y direction in FIG. 3). White portions of these images are fluorescent moieties, indicating ZO-1.

ZO-1 was hardly observed in the cell culture module after 2 days of cell culture, but ZO-1 in a reticular pattern was observed in the cell culture module after 5 days of cell culture. This result confirmed that the endothelial cells were bound through tight junctions in the cell culture module after 5 days of cell culture.

Barrier Function Evaluation Experiment 1

Transepithelial electrical resistance (TEER), which is used as an index for evaluation of the barrier function of endothelial cells, was measured.

Endothelial cells, pericytes, and astrocytes in a cell culture module were cultured for 5 days in the same manner as in "Cell Culture and Observation Experiment". This cell culture module was placed in a TEER measurement vessel, and TEER was measured. The TEER measurement vessel was formed from silicone rubber (PDMS) and had a flow path having the same width as that of the cell culture module. This vessel was in a form that permits electrodes to be respectively inserted into the flow path at opposite sides of the cell culture module in a length direction of the flow path. FIGS. 23(*a*) and 23(*b*) are each an image of the TEER measurement vessel having the cell culture module therein.

The measured TEER was approximately 470 &cm². This result confirmed that a blood-brain barrier (BBB) model formed by the cultured endothelial cells, pericytes, and astrocytes restricted ion permeation, confirming that this BBB model has an excellent barrier function. Note that a BBB model formed using conventional transwell has a TEER of approximately 200 $\Omega \cdot$cm².

Barrier Function Evaluation Experiment 2

A cell culture module including neurons such as shown in FIGS. 6 and 7 was produced.

Specifically, a cubic polycarbonate three-dimensional frame having a side length of 5 mm was prepared, and a 1.5% agarose gel was poured into an opening of the three-dimensional frame and gelled to form a film-shaped window from the resulting hydrogel. The window was formed on each of five faces of the three-dimensional frame as described above. Thereafter, a clump of neurons differentiated from human brain-derived neural stem cells and Matrigel (registered trademark) being an un-gelled culture gel were injected into a cubic space within the three-dimensional frame, and the culture gel was gelled. Then, a hydrogel window was formed on a remaining face of the three-dimensional frame. Through the above, the cell culture module including neurons was produced. This cell culture module was immersed in a culture solution, so that the neurons were cultured for 2 days.

Endothelial cells, pericytes, and astrocytes in a cell culture module were cultured for 5 days in the same manner as in "Cell Culture and Observation Experiment", producing a cell culture module having a BBB model.

An experiment was conducted for evaluation of the barrier function of the BBB model. Specifically, the cell culture module having the BBB model was set in the first accommodation section of the fluidic device produced in the "Fluidic Device Production Experiment", and the cell culture module including the cultured neurons was set in the second accommodation section. The fluidic device was placed in a small-size incubator placeable under a microscope and observable with cells being cultured therein. Thereafter, a fluorescent dye solution (200 µM of Lucifer Yellow) was caused to flow through the first flow path, and a medium solely for neurons was caused to flow through the second flow path. After the fluorescent dye solution and the medium had flowed for 5 minutes (300 seconds), a fluorescence image and a phase-contrast image of the inside of the cell culture module were captured through the fluidic device.

The first flow path simulates a blood vessel outside the BBB, and the second flow path simulates the brain inside the BBB.

A control experiment was also conducted. Specifically, a cubic polycarbonate three-dimensional frame having a side length of 3 mm was prepared, and a 1.5% agarose gel was poured into an opening of the three-dimensional frame and gelled to form a film-shaped window from the resulting hydrogel. Silicone rubber windows were respectively formed on four side faces of the three-dimensional frame by pouring liquid PDMS into the openings of the three-dimensional frame and curing the PDMS. Then, an agarose gel was poured into a cubic space within the three-dimensional frame and gelled. The module (control module) produced as described above was set in the first accommodation section of the fluidic device produced in "Fluidic Device Production Experiment" (with the silicone rubber windows opposed to the flow path wall of the third flow path), and the cell culture module including the cultured neurons was set in the second accommodation section. The fluidic device was placed in a small-size incubator placeable under a microscope and observable with cells being cultured therein. Thereafter, a fluorescent dye solution (200 µM of Lucifer Yellow) was caused to flow through the first flow path, and a medium solely for neurons was caused to flow through the second flow path. After the fluorescent dye solution and the medium had flowed for 5 minutes (300 seconds), a fluorescence image and a phase-contrast image of the inside of the cell culture module were captured through the fluidic device. Note that in the control experiment, the images of the inside of the cell culture module were captured with the same exposure level as in the experiment for the evaluation of the barrier function of the BBB model.

FIGS. 24(*a*) and 24(*b*) each show a fluorescence image (left) of the inside of the cell culture module including neurons used in the control experiment, and an image (right) obtained by superimposing the fluorescence image and a phase-contrast image on one another. The images of the inside of the cell culture module in FIG. 24(*a*) are those that were captured before the cell culture module was set in the fluidic device. The images of the inside of the cell culture module in FIG. 24(*b*) are those that were captured after the fluorescent dye solution and the medium had flowed for 5 minutes (300 seconds). A white portion of the image on the left side of FIG. 24(*b*) is a fluorescent moiety, indicating the fluorescent dye. FIG. 26 is a graph showing relative luminance values on a dashed line x-x' in the image on the left side of FIG. 24(*b*) and relative luminance values on a dashed line x-x' in the image on the left side of FIG. 25(*b*). In FIG. 26, relative luminance value difference corresponds to Lucifer Yellow concentration difference.

The images shown in FIGS. 24(*a*) and 24(*b*), and the graph in FIG. 26 confirmed that in the control experiment, the fluorescent dye contained in the fluorescent dye solution caused to flow through the first flow path passed through the control module, and a major amount of fluorescent dye reached the neurons in the cell culture module in the second accommodation section.

FIGS. 25(*a*) and 25(*b*) each show a fluorescence image (left) of the inside of the cell culture module including neurons used in the experiment for the evaluation of the barrier function of the BBB model, and an image (right) obtained by superimposing the fluorescence image and a phase-contrast image on one another. The images of the inside of the cell culture module in FIG. 25(*a*) are those that were captured before the cell culture module was set in the fluidic device. The images of the inside of the cell culture module in FIG. 25(*b*) are those that were captured after the fluorescent dye solution and the medium had flowed for 5 minutes (300 seconds). The fluorescent dye having reached the cell culture module including neurons, if any, appears as a white portion of the fluorescent image.

Comparison between FIG. 25(*a*) and FIG. 25(*b*) confirmed that the images in FIG. 25(*b*) are very slightly whiter than the images in FIG. 25(*a*). Furthermore, the dashed line x-x' in FIG. 25(*b*) had a relative luminance value of approximately 0.1 as shown in the graph in FIG. 26. That is, a minor amount of fluorescent dye flowed from the first flow path into the cell culture module in the second accommodation section, but this amount was much less than in the control experiment. This result confirmed that the barrier function of the BBB model works for restricting the fluorescent dye from flowing from the first flow path into the cell culture module in the second accommodation section. The result also confirmed that the function of the BBB model formed in the cell culture module is comparable to that of a BBB in vivo, which significantly restricts substances present in bloodstreams from migrating into the brain.

DESCRIPTION OF REFERENCE SIGNS

2 Base
3 Lid member
4 First flow path
5, 5a, 5b Second flow path
6, 6a, 6b Third flow path
7, 7a, 7b First accommodation section
8, 8a, 8b Second accommodation section
9 Third accommodation section
10 Fourth accommodation section
11, 11a, 11b First cell culture module
12, 12a, 12b Second cell culture module
13 Third cell culture module
15 Humoral factor detection module
16 First cell
17 Second cell
18 Third cell
21 First culture gel
22 Second culture gel
23 Third culture gel
25 Three-dimensional frame
26a, 26b Window
31, 32a, 31b, 31c Inlet
32, 32a, 32b, 32c Outlet
35 Cerebrovascular endothelial cell
36 Pericyte
37 Astrocyte
38 Neuron
39 Immune cell
40 Intestinal epithelial cell
41 Hepatocyte
42 Renal cell
44 Antibody-containing bead
50 Fluidic device

What is claimed is:
1. A fluidic device comprising a base and a lid member, wherein
the base and the lid member are configured to form a first flow path, a second flow path, and a third flow path between the base and the lid member, the base and the lid member being bonded to each other, the first flow path communicating with the second flow path through the third flow path, and

a first cell culture module and a second cell culture module,
wherein the third flow path has a first accommodation section configured to detachably accommodate the first cell culture module,
the second flow path has a second accommodation section configured to detachably accommodate the second cell culture module,
the first cell culture module contains first cells having a barrier function and a first culture gel, and has a light-permeable first window formed from a hydrogel or a porous body,
the second cell culture module contains second cells and a second culture gel, and has a light-permeable second window formed from a hydrogel or a porous body,
the first accommodation section is configured in such a manner that the first cell culture module blocks the third flow path,
the first cell culture module includes a three-dimensional frame,
the first window closes at least one first opening bordered by the three-dimensional frame,
the first cells or a cellular tissue containing the first cells closes a second opening bordered by the three-dimensional frame and is in contact with the three-dimensional frame, and
the first cell culture module is accommodated in the first accommodation section in such a manner that the first cells or the cellular tissue containing the first cells is opposed to the first flow path.
2. The fluidic device according to claim 1, wherein the first accommodation section is configured in such a manner that the first cells or the cellular tissue containing the first cells is exposed to a flow in the first flow path.
3. The fluidic device according to claim 1, wherein the first cells or the cellular tissue containing the first cells has a filtering function.
4. The fluidic device according to claim 1, wherein
the first cell culture module has a third window formed from a light-permeable resin,
the third window closes at least one third opening bordered by the three-dimensional frame, and
the first cell culture module is accommodated in the first accommodation section in such a manner that the third window faces to a flow path wall of the third flow path.
5. The fluidic device according to claim 1, wherein the first cells are any of vascular endothelial cells, intestinal epithelial cells, and epidermal cells.
6. The fluidic device according to claim 1, wherein the first cell culture module includes a blood-brain barrier model including vascular endothelial cells, pericytes, and astrocytes.
7. The fluidic device according to claim 1, wherein
the light-permeable first window is formed from
the hydrogel including at least one of an agarose gel, a polyacrylamide gel, sodium alginate, or a collagen gel, or
the porous body including at least one of a porous material sheet, a mesh, an etching sheet, a non-woven fabric, or a woven fabric, and
the light-permeable second window is formed from
the hydrogel including at least one of an agarose gel, a polyacrylamide gel, sodium alginate, or a collagen gel, or
the porous body including at least one of a porous material sheet, a mesh, an etching sheet, a non-woven fabric, or a woven fabric.

8. The fluidic device according to claim 1, wherein the third flow path has the same width as the first cell culture module in the first accommodation section.

9. The fluidic device according to claim 1, wherein the first accommodation section is configured in such a manner that the first cell culture module is adjacent to the first flow path.

10. The fluidic device according to claim 1, wherein the second accommodation section is configured in such a manner that the second cell culture module is located at a confluence of the second flow path and the third flow path.

11. The fluidic device according to claim 1, wherein the second flow path has a third accommodation section configured to detachably accommodate a third cell culture module, and the third cell culture module contains third cells and a third culture gel, and has a light-permeable fourth window formed from a hydrogel or a porous body.

12. The fluidic device according to claim 1, wherein the second flow path has a fourth accommodation section configured to detachably accommodate a humoral factor detection module.

* * * * *